(12) United States Patent
Dowling et al.

(10) Patent No.: US 7,764,026 B2
(45) Date of Patent: Jul. 27, 2010

(54) SYSTEMS AND METHODS FOR DIGITAL ENTERTAINMENT

(75) Inventors: Kevin J. Dowling, Westford, MA (US); Ian Lane Davis, North Andover, MA (US); George G. Mueller, Boston, MA (US); Ihor A. Lys, Boston, MA (US)

(73) Assignee: Philips Solid-State Lighting Solutions, Inc., Burlington, MA (US)

( * ) Notice: Subject to any disclaimer, the term of this patent is extended or adjusted under 35 U.S.C. 154(b) by 1916 days.

(21) Appl. No.: 10/045,604

(22) Filed: Oct. 23, 2001

(65) Prior Publication Data

US 2003/0057884 A1 Mar. 27, 2003

Related U.S. Application Data

(63) Continuation-in-part of application No. 09/923,223, filed on Aug. 6, 2001, now abandoned, and a continuation-in-part of application No. 09/917,246, filed on Jul. 27, 2001, now Pat. No. 6,888,322, and a continuation-in-part of application No. 09/886,958, filed on Jun. 21, 2001, now Pat. No. 7,228,190, and a continuation-in-part of application No. 09/815,418, filed on Mar. 22, 2001, now Pat. No. 6,577,080, and a continuation-in-part of application No. 09/805,590, filed on Mar. 13, 2001, now Pat. No. 7,064,498, and a continuation-in-part of application No. 09/805,368, filed on Mar. 13, 2001, now Pat. No. 7,186,003, and a continuation-in-part of application No. 09/742,017, filed on Dec. 20, 2000, now abandoned, and a continuation-in-part of application No. 09/626,905, filed on Jul. 27, 2000, now Pat. No. 6,340,868, and a continuation-in-part of application No. 09/333,739, filed on Jun. 15, 1999, now Pat. No. 7,352,339, and a continuation-in-part of application No. 09/213,189, filed on Dec. 17, 1998, now Pat. No. 6,459,919, and a continuation-in-part of application No. 09/213,581, filed on Dec. 17, 1998, now Pat. No. 7,038,398, and a continuation-in-part of application No. 09/213,540, filed on Dec. 17, 1998, now Pat. No. 6,720,745, which is a continuation of application No. 09/213,548, filed on Dec. 17, 1998, now Pat. No. 6,166,496, and a continuation-in-part of application No. 09/215,624, filed on Dec. 17, 1998, now Pat. No. 6,528,954.

(60) Provisional application No. 60/277,911, filed on Mar. 22, 2001, provisional application No. 60/268,259, filed on Feb. 13, 2001, provisional application No. 60/262,153, filed on Jan. 17, 2001, provisional application No. 60/262,022, filed on Jan. 16, 2001, provisional application No. 60/243,250, filed on Oct. 25, 2000, provisional application No. 60/242,484, filed on Oct. 23, 2000, provisional application No. 60/090,920, filed on Jun. 26, 1998, provisional application No. 60/079,285, filed on Mar. 25, 1998, provisional application No. 60/078,861, filed on Mar. 20, 1998, provisional application No. 60/068,792, filed on Dec. 24, 1997, provisional application No. 60/071,281, filed on Dec. 17, 1997.

(51) Int. Cl.
*G05F 1/00* (2006.01)

(52) U.S. Cl. ..................................................... 315/307

(58) Field of Classification Search ................. 345/420, 345/473; 386/68, 81, 95, 125; 463/32, 30; 315/169.1, 169.2, 169.3, 169.4, 291, 307
See application file for complete search history.

(56) References Cited

U.S. PATENT DOCUMENTS

| | | |
|---|---|---|
| 2,909,097 A | 10/1959 | Alden et al. |
| 3,318,185 A | 5/1967 | Kott |
| 3,561,719 A | 2/1971 | Grindle |
| 3,586,936 A | 6/1971 | McLeroy |
| 3,601,621 A | 8/1971 | Ritchie |
| 3,643,088 A | 2/1972 | Osteen et al. |
| 3,746,918 A | 7/1973 | Drucker et al. |
| 3,818,216 A | 6/1974 | Larraburu |
| 3,832,503 A | 8/1974 | Crane |
| 3,858,086 A | 12/1974 | Anderson et al. |

| Patent | Date | Name |
|---|---|---|
| 3,909,670 A | 9/1975 | Wakamatsu et al. |
| 3,924,120 A | 12/1975 | Cox, III |
| 3,958,885 A | 5/1976 | Stockinger et al. |
| 3,974,637 A | 8/1976 | Bergey et al. |
| 4,001,571 A | 1/1977 | Martin |
| 4,054,814 A | 10/1977 | Fegley et al. |
| 4,082,395 A | 4/1978 | Donato et al. |
| 4,096,349 A | 6/1978 | Donato |
| 4,241,295 A | 12/1980 | Williams, Jr. |
| 4,272,689 A | 6/1981 | Crosby et al. |
| 4,273,999 A | 6/1981 | Pierpoint |
| 4,298,869 A | 11/1981 | Okuno |
| 4,329,625 A | 5/1982 | Nishizawa et al. |
| 4,367,464 A | 1/1983 | Kurahashi et al. |
| 4,388,567 A | 6/1983 | Yamazaki et al. |
| 4,388,589 A | 6/1983 | Molldrem, Jr. |
| 4,392,187 A | 7/1983 | Bornhorst |
| 4,420,711 A | 12/1983 | Takahashi et al. |
| 4,500,796 A | 2/1985 | Quin |
| 4,622,881 A | 11/1986 | Rand |
| 4,625,152 A | 11/1986 | Nakai |
| 4,635,052 A | 1/1987 | Aoike et al. |
| 4,647,217 A | 3/1987 | Havel |
| 4,656,398 A | 4/1987 | Michael et al. |
| 4,668,895 A | 5/1987 | Schneiter |
| 4,682,079 A | 7/1987 | Sanders et al. |
| 4,686,425 A | 8/1987 | Havel |
| 4,687,340 A | 8/1987 | Havel |
| 4,688,154 A | 8/1987 | Nilssen |
| 4,688,869 A | 8/1987 | Kelly |
| 4,695,769 A | 9/1987 | Schweickardt |
| 4,701,669 A | 10/1987 | Head et al. |
| 4,705,406 A | 11/1987 | Havel |
| 4,707,141 A | 11/1987 | Havel |
| 4,727,289 A | 2/1988 | Uchida |
| 4,740,882 A | 4/1988 | Miller |
| 4,753,148 A | 6/1988 | Johnson |
| 4,771,274 A | 9/1988 | Havel |
| 4,780,621 A | 10/1988 | Bartleucci et al. |
| 4,818,072 A | 4/1989 | Mohebban |
| 4,837,565 A | 6/1989 | White |
| 4,843,627 A | 6/1989 | Stebbins |
| 4,845,481 A | 7/1989 | Havel |
| 4,845,745 A | 7/1989 | Havel |
| 4,863,223 A | 9/1989 | Weissenbach et al. |
| 4,874,320 A | 10/1989 | Freed et al. |
| 4,887,074 A | 12/1989 | Simon et al. |
| 4,922,154 A | 5/1990 | Cacoub |
| 4,934,852 A | 6/1990 | Havel |
| 4,962,687 A | 10/1990 | Belliveau et al. |
| 4,965,561 A | 10/1990 | Havel |
| 4,973,835 A | 11/1990 | Kurosu et al. |
| 4,979,081 A | 12/1990 | Leach et al. |
| 4,980,806 A | 12/1990 | Taylor et al. |
| 4,992,704 A | 2/1991 | Stinson |
| 5,003,227 A | 3/1991 | Nilssen |
| 5,008,595 A | 4/1991 | Kazar |
| 5,010,459 A | 4/1991 | Taylor et al. |
| 5,027,262 A | 6/1991 | Freed |
| 5,034,807 A | 7/1991 | Von Kohorn |
| 5,051,935 A * | 9/1991 | Matty .................. 702/178 |
| 5,072,216 A | 12/1991 | Grange |
| 5,078,039 A | 1/1992 | Tulk et al. |
| 5,083,063 A | 1/1992 | Brooks |
| 5,126,634 A | 6/1992 | Johnson |
| 5,128,595 A | 7/1992 | Hara |
| 5,134,387 A | 7/1992 | Smith et al. |
| 5,142,199 A | 8/1992 | Elwell |
| 5,154,641 A | 10/1992 | McLaughlin |
| 5,164,715 A | 11/1992 | Kashiwabara et al. |
| 5,184,114 A | 2/1993 | Brown |
| 5,194,854 A | 3/1993 | Havel |
| 5,209,560 A | 5/1993 | Taylor et al. |
| 5,225,765 A | 7/1993 | Callahan et al. |
| 5,226,723 A | 7/1993 | Chen |
| 5,254,910 A | 10/1993 | Yang |
| 5,256,948 A | 10/1993 | Boldin et al. |
| 5,282,121 A | 1/1994 | Bornhorst et al. |
| 5,294,865 A | 3/1994 | Haraden |
| 5,307,295 A | 4/1994 | Taylor et al. |
| 5,329,431 A | 7/1994 | Taylor et al. |
| 5,350,977 A | 9/1994 | Hamamoto et al. |
| 5,357,170 A | 10/1994 | Luchaco et al. |
| 5,371,618 A | 12/1994 | Tai et al. |
| 5,374,876 A | 12/1994 | Horibata et al. |
| 5,375,043 A | 12/1994 | Tokunaga |
| 5,388,357 A | 2/1995 | Malita |
| 5,402,702 A | 4/1995 | Hata |
| 5,404,282 A | 4/1995 | Klinke et al. |
| 5,406,176 A | 4/1995 | Sugden |
| 5,410,328 A | 4/1995 | Yoksza et al. |
| 5,412,284 A | 5/1995 | Moore et al. |
| 5,412,552 A | 5/1995 | Fernandes |
| 5,420,482 A | 5/1995 | Phares |
| 5,421,059 A | 6/1995 | Leffers, Jr. |
| 5,432,408 A | 7/1995 | Matsuda et al. |
| 5,436,535 A | 7/1995 | Yang |
| 5,461,188 A | 10/1995 | Drago et al. |
| 5,463,280 A | 10/1995 | Johnson |
| 5,465,144 A | 11/1995 | Parker et al. |
| 5,475,364 A * | 12/1995 | Kenet .................. 340/522 |
| 5,489,827 A | 2/1996 | Xia |
| 5,491,402 A | 2/1996 | Small |
| 5,504,395 A | 4/1996 | Johnson et al. |
| 5,519,809 A * | 5/1996 | Husseiny et al. .......... 704/275 |
| 5,545,950 A | 8/1996 | Cho |
| 5,561,346 A | 10/1996 | Byrne |
| 5,575,459 A | 11/1996 | Anderson |
| 5,575,554 A | 11/1996 | Guritz |
| 5,592,051 A | 1/1997 | Korkala |
| 5,640,061 A | 6/1997 | Bornhorst et al. |
| 5,642,129 A | 6/1997 | Zavracky et al. |
| 5,662,403 A * | 9/1997 | Akashi et al. .............. 362/558 |
| 5,673,059 A | 9/1997 | Zavracky et al. |
| 5,701,058 A | 12/1997 | Roth |
| 5,721,471 A | 2/1998 | Begemann et al. |
| 5,734,590 A | 3/1998 | Tebbe |
| 5,751,118 A | 5/1998 | Mortimer |
| 5,752,766 A | 5/1998 | Bailey et al. |
| 5,769,527 A | 6/1998 | Taylor et al. |
| 5,774,098 A | 6/1998 | Kawashima et al. |
| 5,803,579 A | 9/1998 | Turnbull et al. |
| 5,808,689 A | 9/1998 | Small |
| 5,821,695 A | 10/1998 | Vilanilam et al. |
| 5,838,308 A * | 11/1998 | Knapp et al. ................ 345/173 |
| 5,848,837 A | 12/1998 | Gustafson |
| 5,850,126 A | 12/1998 | Kanbar |
| 5,851,063 A | 12/1998 | Doughty et al. |
| 5,852,658 A | 12/1998 | Knight et al. |
| RE36,030 E | 1/1999 | Nadeau |
| 5,859,508 A | 1/1999 | Ge et al. |
| 5,886,701 A * | 3/1999 | Chauvin et al. ............. 345/418 |
| 5,895,986 A | 4/1999 | Walters et al. |
| 5,896,010 A | 4/1999 | Mikolajczak et al. |
| 5,896,457 A | 4/1999 | Tyrrel |
| 5,912,653 A | 6/1999 | Fitch |
| 5,923,363 A | 7/1999 | Elberbaum |
| 5,924,784 A | 7/1999 | Chliwnyj et al. |
| 5,926,168 A * | 7/1999 | Fan .......................... 345/158 |
| 5,938,772 A | 8/1999 | Welch |
| 5,945,988 A | 8/1999 | Williams et al. |
| 5,946,209 A | 8/1999 | Eckel et al. |
| 5,952,680 A | 9/1999 | Strite |
| 5,959,547 A | 9/1999 | Tubel et al. |
| 5,963,185 A | 10/1999 | Havel |
| 5,974,262 A * | 10/1999 | Fuller et al. .................. 710/18 |

| | | |
|---|---|---|
| 5,974,553 A | 10/1999 | Gandar |
| 5,999,185 A * | 12/1999 | Kato et al. .................. 345/420 |
| 6,008,783 A | 12/1999 | Kitagawa et al. |
| 6,011,546 A * | 1/2000 | Bertram ..................... 715/700 |
| 6,012,980 A * | 1/2000 | Yoshida et al. ................. 463/2 |
| 6,016,038 A | 1/2000 | Mueller et al. |
| 6,018,237 A | 1/2000 | Havel |
| 6,018,332 A | 1/2000 | Nason et al. |
| 6,020,825 A | 2/2000 | Chansky et al. |
| 6,025,550 A | 2/2000 | Kato |
| 6,031,343 A | 2/2000 | Recknagel et al. |
| 6,068,383 A | 5/2000 | Robertson et al. |
| 6,072,280 A | 6/2000 | Allen |
| 6,087,776 A | 7/2000 | Yamashita et al. |
| 6,095,661 A | 8/2000 | Lebens et al. |
| 6,097,352 A | 8/2000 | Zavracky et al. |
| 6,132,072 A | 10/2000 | Turnbull et al. |
| 6,135,604 A | 10/2000 | Lin |
| 6,150,774 A | 11/2000 | Mueller et al. |
| 6,166,496 A | 12/2000 | Lys et al. |
| 6,166,718 A * | 12/2000 | Takeda ....................... 715/856 |
| 6,183,086 B1 | 2/2001 | Neubert |
| 6,184,628 B1 | 2/2001 | Ruthenberg |
| 6,196,471 B1 | 3/2001 | Ruthenberg |
| 6,211,626 B1 | 4/2001 | Lys et al. |
| 6,215,409 B1 | 4/2001 | Blach |
| 6,227,973 B1 * | 5/2001 | Kikuchi ....................... 463/31 |
| 6,250,774 B1 | 6/2001 | Begemann et al. |
| 6,289,466 B1 | 9/2001 | Bayramoglu et al. |
| 6,292,901 B1 | 9/2001 | Lys et al. |
| 6,304,287 B1 * | 10/2001 | Nagata ....................... 348/53 |
| 6,340,868 B1 | 1/2002 | Lys et al. |
| 6,379,244 B1 | 4/2002 | Sagawa et al. |
| 6,408,128 B1 * | 6/2002 | Abecassis ..................... 386/68 |
| 6,459,919 B1 | 10/2002 | Lys et al. |
| 6,476,726 B1 | 11/2002 | Pederson |
| 6,486,873 B1 | 11/2002 | McDonough et al. |
| 6,492,908 B1 | 12/2002 | Cheng |
| 6,494,593 B2 | 12/2002 | An et al. |
| 6,528,954 B1 | 3/2003 | Lys et al. |
| 6,542,155 B1 * | 4/2003 | Mifune et al. ................. 345/428 |
| 6,548,967 B1 | 4/2003 | Dowling et al. |
| 6,553,178 B2 * | 4/2003 | Abecassis ..................... 386/83 |
| 6,560,707 B2 * | 5/2003 | Curtis et al. ................. 713/163 |
| 6,564,108 B1 | 5/2003 | Makar et al. |
| 6,577,080 B2 | 6/2003 | Lys et al. |
| 6,608,453 B2 | 8/2003 | Morgan et al. |
| 6,608,996 B1 | 8/2003 | Laurikka et al. |
| 6,611,297 B1 | 8/2003 | Akashi et al. |
| 6,624,597 B2 | 9/2003 | Dowling et al. |
| 6,717,376 B2 | 4/2004 | Lys et al. |
| 6,720,745 B2 | 4/2004 | Lys et al. |
| 6,868,292 B2 | 3/2005 | Ficco et al. |
| 7,015,825 B2 | 3/2006 | Callahan |
| 2001/0033488 A1 | 10/2001 | Chliwnyj et al. |
| 2002/0004423 A1 | 1/2002 | Minami et al. |
| 2002/0038157 A1 | 3/2002 | Dowling et al. |
| 2002/0044066 A1 | 4/2002 | Dowling et al. |
| 2002/0047569 A1 | 4/2002 | Dowling et al. |
| 2002/0048169 A1 | 4/2002 | Dowling et al. |
| 2002/0057061 A1 | 5/2002 | Mueller et al. |
| 2002/0070688 A1 | 6/2002 | Dowling et al. |
| 2002/0074559 A1 | 6/2002 | Dowling et al. |
| 2002/0078221 A1 | 6/2002 | Blackwell et al. |
| 2002/0101197 A1 | 8/2002 | Lys et al. |
| 2002/0130627 A1 | 9/2002 | Dowling et al. |
| 2002/0145394 A1 | 10/2002 | Morgan et al. |
| 2002/0145869 A1 | 10/2002 | Dowling |
| 2002/0152045 A1 | 10/2002 | Dowling et al. |
| 2002/0153851 A1 | 10/2002 | Dowling et al. |
| 2002/0158583 A1 | 10/2002 | Lys et al. |
| 2002/0163316 A1 | 11/2002 | Dowling et al. |
| 2002/0171365 A1 | 11/2002 | Morgan et al. |
| 2002/0171377 A1 | 11/2002 | Mueller et al. |
| 2002/0171378 A1 | 11/2002 | Morgan et al. |
| 2002/0176259 A1 | 11/2002 | Ducharme |
| 2002/0195975 A1 | 12/2002 | Dowling et al. |
| 2003/0011538 A1 | 1/2003 | Lys et al. |
| 2003/0028260 A1 | 2/2003 | Blackwell |
| 2003/0057884 A1 | 3/2003 | Dowling et al. |
| 2003/0057886 A1 | 3/2003 | Lys et al. |
| 2003/0057887 A1 | 3/2003 | Dowling et al. |
| 2003/0057890 A1 | 3/2003 | Lys et al. |
| 2003/0076281 A1 | 4/2003 | Morgan et al. |
| 2003/0100837 A1 | 5/2003 | Lys et al. |
| 2003/0133292 A1 | 7/2003 | Mueller et al. |
| 2003/0137258 A1 | 7/2003 | Piepgras et al. |
| 2003/0222587 A1 | 12/2003 | Dowling et al. |
| 2004/0032226 A1 | 2/2004 | Lys |
| 2004/0036006 A1 | 2/2004 | Dowling |
| 2004/0052076 A1 | 3/2004 | Mueller et al. |
| 2004/0090191 A1 | 5/2004 | Mueller et al. |
| 2004/0090787 A1 | 5/2004 | Dowling et al. |
| 2004/0105261 A1 | 6/2004 | Ducharme et al. |
| 2004/0113568 A1 | 6/2004 | Dowling et al. |
| 2004/0116039 A1 | 6/2004 | Mueller et al. |
| 2004/0130909 A1 | 7/2004 | Mueller et al. |
| 2004/0156192 A1 | 8/2004 | Kerr et al. |
| 2004/0178751 A1 | 9/2004 | Mueller et al. |
| 2004/0212320 A1 | 10/2004 | Dowling et al. |
| 2004/0212321 A1 | 10/2004 | Lys et al. |
| 2004/0212993 A1 | 10/2004 | Morgan et al. |
| 2004/0240890 A1 | 12/2004 | Lys et al. |
| 2004/0257007 A1 | 12/2004 | Lys et al. |
| 2006/0053447 A1 | 3/2006 | Krzyzanowski et al. |
| 2006/0064533 A1 | 3/2006 | Rael et al. |

FOREIGN PATENT DOCUMENTS

| | | |
|---|---|---|
| AU | 6 267 9 | 12/1996 |
| CA | 2 178 432 | 12/1996 |
| DE | 101 37 919 A1 | 6/2002 |
| EP | 0495305 A2 | 7/1992 |
| EP | 0 564 127 A2 | 10/1993 |
| EP | 0534710 B1 | 1/1996 |
| EP | 0752632 A2 | 1/1997 |
| EP | 0752632 A3 | 8/1997 |
| EP | 0823812 A2 | 2/1998 |
| EP | 0 903 169 A2 | 3/1999 |
| EP | 0935234 A1 | 8/1999 |
| EP | 0942631 A2 | 9/1999 |
| EP | 1020352 A2 | 7/2000 |
| EP | 1113215 A2 | 7/2001 |
| EP | 1 130 554 A2 | 9/2001 |
| FR | 88 17359 | 12/1998 |
| GB | 2045098 A | 10/1980 |
| GB | 2135536 A | 8/1984 |
| GB | 2176042 A | 12/1986 |
| GB | 2327047 A | 1/1999 |
| GB | 2354602 A | 3/2001 |
| JP | 57-157293 | 9/1982 |
| JP | 06043830 | 2/1994 |
| JP | 7-39120 | 7/1995 |
| JP | 8-106264 | 4/1996 |
| JP | 9 320766 | 12/1997 |
| JP | 2000-17383 A | 6/2000 |
| WO | WO 89/05086 | 6/1989 |
| WO | WO 94/18809 | 8/1994 |
| WO | WO 95/13498 | 5/1995 |
| WO | WO 96/41098 | 12/1996 |

OTHER PUBLICATIONS

"LM117/LM317A/LM317 3-Terminal Adjustable Regulator", National Semiconductor Corporation, May 1997, pp. 1-20.
"DS96177 RS-485 / RS-422 Differential Bus Repeater", National Semiconductor Corporation, Feb. 1996, pp. 1-8.

"DS2003 / DA9667 / DS2004 High Current / Voltage Darlington Drivers", National Semiconductor Corporation, Dec. 1995, pp. 1-8.
"LM140A / LMI40 / LM340A / LM7800C Series 3—Terminal Positive Regulators", National Semiconductor Corporation, Jan. 1995, pp. 1-14.
High End Systems, Inc., Trackspot User Manual, Aug. 1997, Excerpts (Cover, Title page, pp. ii through iii and 2-13 through 2-14).
Artistic License, AL4000 DMX512 Processors, Revision 3.4, Jun. 2000, Excerpts (Cover, pp. 7,92 through 102).
Artistic License, Miscellaneous Drawings (3 sheets) Jan. 12, 1995.
Artistic License, Miscellaneous Documents (2 sheets Feb. 1995 and Apr. 1996).
Newnes's Dictionary of Electronics, Fourth Edition, S.W. Amos, et al., Preface to First Edition, pp. 278-279.
"http://www.luminus.cx/projects/chaser", (Nov. 13, 2000), pp. 1-16.
Co-Pending U.S. Appl. No. 09/815,418, filed Mar. 22, 2001, Ihor Lys, et al., entitled "Lighting Entertainment System,".
U.S. Appl. No. 09/989,677, filed Nov. 20, 2001 Claims as Allowed.
U.S. Appl. No. 09/989,677, filed Nov. 20, 2001 Notice of Allowance Dated Apr. 10, 2007.
U.S. Appl. No. 09/989,677, filed Nov. 20, 2001 Office Action Dated Oct. 31, 2006.
U.S. Appl. No. 09/989,677, filed Nov. 20, 2001 Office Action Dated Jul. 27, 2006.
U.S. Appl. No. 09/989,677, filed Nov. 20, 2001 Office Action Dated Jun. 2, 2005.
U.S. Appl. No. 09/989,677, filed Nov. 20, 2001 Notice of Allowance Dated Apr. 22, 2005.
U.S. Appl. No. 09/989,677, filed Nov. 20, 2001 Office Action Dated Jul. 27, 2004.
U.S. Appl. No. 09/989,677, filed Nov. 20, 2001 Office Action Dated Mar. 26, 2004.
Japanese Application Serial No. 2002-546469 filed Nov. 20, 2001 Claims as Pending.
Japanese Application Serial No. 2002-546469 filed Nov. 20, 2001 Office Action Dated Mar. 20, 2007.
U.S. Appl. No. 10/951,122, filed Sep. 27, 2004 Office Action dated May 15, 2007.

\* cited by examiner

*Primary Examiner*—Douglas W Owens
*Assistant Examiner*—Minh D A
(74) *Attorney, Agent, or Firm*—Wolf Greenfield LLP

(57) ABSTRACT

In computer games, there is typically a display that represents a view into a virtual world of some type. There is also typically a user in a real world environment that surrounds the display screen interacting with the virtual world. Disclosed herein are systems and methods for using lighting systems, in particular LED based lighting systems, to allow a user to receive information from the virtual world in coordination with, in addition to, and/or instead of the information received from the display.

48 Claims, 13 Drawing Sheets

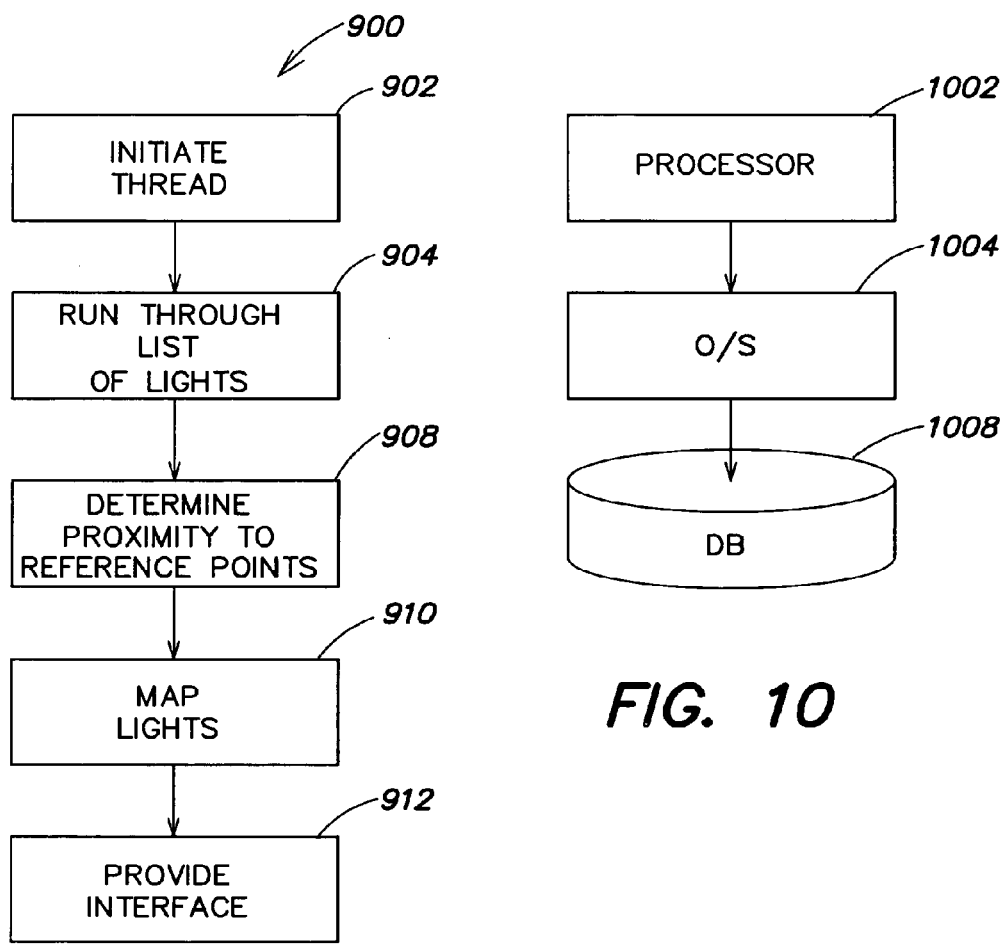

| LIGHT | POSITION | DIRECTION | γ | ATTRIBUTE₁ | ATTRIBUTE N |
|---|---|---|---|---|---|
| L1001 | P1001 | D1001 | γ1001 | ... | ... |
| L1002 | P1002 | D1002 | γ1002 | ... | ... |
| L1003 | P1003 | D1005 | γ1003 | ... | ... |
| L1004 | P1004 | D1008 | γ1004 | ... | ... |
| L1005 | P1005 | D1001 | γ1005 | ... | ... |

FIG. 11

SYSTEMS AND METHODS FOR DIGITAL ENTERTAINMENT

CROSS REFERENCE TO RELATED APPLICATIONS

This application claims the benefit under 35 U.S.C. §119 (e) of the following U.S. provisional patent applications:

Ser. No. 60/243,250, filed Oct. 25, 2000, entitled "Illumination of Liquids;"

Ser. No. 60/262,153, filed Jan. 17, 2001, entitled "Information Systems;"

Ser. No. 60/242,484, filed Oct. 23, 2000, entitled "Systems and Methods for Digital Entertainment;"

Ser. No. 60/262,022, filed Jan. 16, 2001, entitled "Color Changing LCD Screens;"

Ser. No. 60/268,259, filed Feb. 13, 2001, entitled "LED-Based Lighting Systems and Methods for Vehicles;" and Ser. No. 60/277,911, filed Mar. 22, 2001, entitled "Systems and Methods for Digital Entertainment."

This application also claims the benefit under 35 U.S.C. §120 as a continuation-in-part (CIP) of the following U.S. Patent Applications:

Ser. No. 09/215,624, filed Dec. 17, 1998 now U.S. Pat. No. 6,528,954, entitled "Smart Light Bulb;"

Ser. No. 09/213,607, filed Dec. 17, 1998 now abandoned, entitled "Systems and Methods for Sensor-Responsive Illumination;"

Ser. No. 09/213,189, filed Dec. 17, 1998 now U.S. Pat. No. 6,459,919, entitled "Precision Illumination Methods and Systems;"

Ser. No. 09/213,581, filed Dec. 17, 1998 now U.S. Pat. No. 7,038,398, entitled "Kinetic Illumination Methods and Systems;"

Ser. No. 09/213,540, filed Dec. 17, 1998 now U.S. Pat. No. 6,720,745, entitled "Data Delivery Track;"

Ser. No. 09/333,739, filed Jun. 15, 1999 now U.S. Pat. No. 7,352,339, entitled "Diffuse Illumination Methods and Systems;"

Ser. No. 09/626,905, filed Jul. 27, 2000, entitled "Illumination Components," now U.S. Pat. No. 6,340,868, issued Jan. 22, 2002;

Ser. No. 09/742,017, filed Dec. 20, 2000 now abandoned, entitled "Lighting Entertainment System," which is a continuation of U.S. Ser. No. 09/213,548, filed Dec. 17, 1998, now U.S. Pat. No. 6,166,496, issued Dec. 26, 2000;

Ser. No. 09/616,214, filed Jul. 14, 2000 now U.S. Pat. No. 7,139,617, entitled "Systems and Methods for Authoring Lighting Sequences;"

Ser. No. 09/815,418, filed Mar. 22, 2001 now U.S. Pat. No. 6,577,080, entitled "Lighting Entertainment System," which also is a continuation of U.S. Ser. No. 09/213,548, filed Dec. 17, 1998, now U.S. Pat. No. 6,166,496, issued Dec. 26, 2000;

Ser. No. 09/805,368, filed Mar. 13, 2001 now U.S. Pat. No. 7,186,003, entitled "Light Emitting Diode Based Products;"

Ser. No. 09/805,590, filed Mar. 13, 2001 now U.S. Pat. No. 7,064,498, entitled "Light Emitting Diode Based Products;"

Ser. No. 09/917,246, entitled "Systems and Methods for Color Changing Device and Enclosure," filed Jul. 27, 2001 now U.S. Pat. No. 6,888,322;

Ser. No. 09/923,223, entitled "Ultraviolet Light Emitting Diode Systems and Methods," filed Aug. 6, 2001 now abandoned; and Ser. No. 09/886,958, entitled "Method and Apparatus for Controlling a Lighting System in Response to an Audio Input," filed Jun. 21, 2001 now U.S. Pat. No. 7,228,190.

This application also claims the benefit under 35 U.S.C. §120 of each of the following U.S. Provisional Applications, as at least one of the above-identified U.S. Non-provisional Applications similarly is entitled to the benefit of at least one of the following Provisional Applications:

Ser. No. 60/071,281, filed Dec. 17, 1997, entitled "Digitally Controlled Light Emitting Diodes Systems and Methods;"

Ser. No. 60/068,792, filed Dec. 24, 1997, entitled "Multi-Color Intelligent Lighting;"

Ser. No. 60/078,861, filed Mar. 20, 1998, entitled "Digital Lighting Systems;"

Ser. No. 60/079,285, filed Mar. 25, 1998, entitled "System and Method for Controlled Illumination;" and Ser. No. 60/090,920, filed Jun. 26, 1998, entitled "Methods for Software Driven Generation of Multiple Simultaneous High Speed Pulse Width Modulated Signals."

Each of the foregoing applications is hereby incorporated herein by reference.

BACKGROUND OF THE INVENTION

Computer games are well known, wherein one or more users interact with a computer to play a game, typically involving use of a control device, such as a mouse, joystick or keypad, to move objects that appear on a display screen to accomplish objectives of the game. There are many types of games, including first-person games shooting, strategy games, war games, fighting games, puzzles, and many others. Computer games are played on or use many devices, including televisions, consoles. PDAs, handheld game devices, personal and laptop computers, and others. Some games are run on standalone computers, while others employ networks, such as the Internet and World Wide Web.

The marketplace for computer games is very competitive, and improvements to games are actively sought. Past improvements include enhancements to the graphical or sound quality of games, improvements to systems that run games, such as processing speeds, and introduction of innovative game types. A need exists for further improvements of the computer game experience, including enhancements that take advantage of characteristics of the environment of the game user.

SUMMARY OF THE INVENTION

The present disclosure sets forth improvements to computer games and other computer applications through the coordinated control of lighting systems that illuminate the environment of the user in coordination with the play of a game or the use of an application. In embodiments, the lighting systems disclosed herein change the illumination of the user's real world environment in coordination with events, attributes and objects of a computer game.

In an embodiment there is disclosed a system for imparting information using a lighting system. The system includes a computing device including a video display; a lighting system in communication with the computing device for producing illumination; and a software application for dynamically controlling the illumination in response to or in coordination with information presented on the video display so as to impart information to a user. The software application can include a game and/or objects and may allow for relation of a portion of the lighting system to an object. The information provided by the illumination system can relate to an attribute of an object. The software application can be controlled by a second software application which can also include a game.

In an embodiment, the lighting system can include an LED and/or can include a screen upon which the illumination is projected. This screen can be a cabana. The computing system may also include a video game console.

In an embodiment, the information provided by the lighting system can be different from the information provided on the video display, either by being additive to the information provided on the video display, or duplicative of the information provided on the video display but in a different form. In an embodiment, the video display could provide no information.

In an embodiment there is disclosed a system for controlling a lighting system comprising: lighting system including a lighting fixture, the lighting system in communication with a computing device; and a software application including a software object operating in conjunction with the computing device; wherein, the software application attaches the control of the lighting fixture to the software object. The software application may include a game and the software object may comprise an object in the game. The system could also include a library of effects for use with the lighting system.

In an embodiment there is disclosed a screen for use with a lighting system comprising; a frame designed to be placed in proximity to the user of a computing system and; a material mounted on the frame; wherein the material is arranged in a manner so as to be able to reflect illumination produced by a lighting system to the user of the computing system. This screen may be shaped to form a cabana and/or a portion of a sphere and/or may be formed so as to be repeatedly assembled and disassembled. Further, the computing system may include a video display and the frame may be designed to be placed to at least partially enclose the video display, be placed behind the video display relative to the user, and/or at least partially encloses the computing system and the user.

In an embodiment the screen could further include a mounting bar for the attachment of lighting fixtures to the screen. The mounting bar may be arranged so that the lighting fixtures have a fixed point of attachment to the mounting bar. The mounting bar may alternatively or additively be arranged so that fixtures have a fixed point of projection onto the screen when attached to the mounting bar. Those lighting fixtures may comprise at least a portion of the lighting system.

In an embodiment there is disclosed a software application for use on a computing device comprising: computer code for generating a computer game on a computing device; and computer code for controlling a lighting system in communication with the computing device.

In another embodiment there is disclosed a method for visualizing the relative location of virtual objects within a virtual environment comprising: having a computing device; generating a virtual environment on the computing device, the virtual environment containing a plurality of virtual objects; associating with a virtual object, the illumination from a lighting fixture; and visualizing the relative location of the virtual object by the positioning of the illumination. The visualizing may include the position of the illumination corresponding to the position of the lighting fixture or the position of the illumination corresponding to the position on a surface which is illuminated by the illumination. The position on the surface may perform at least one of the following: reflection of the illumination, refraction of the illumination, absorption and reemission of the illumination.

In another embodiment there is disclosed a method for enhancing the play of a computer game comprising: providing to a user a lighting system; providing to the user software for controlling the lighting system, the software being capable of interfacing with a computer game; and allowing the user to use the software to control the lighting system in a manner that enhances the play of the computer game.

In another embodiment there is disclosed a lighting system for use with a software application comprising: at least one lighting fixture; and a computer application compatible with the software application, the computer application allowing for the software application to provide information to a user through illumination generated by the lighting fixture. The computer application may include computer software and/or computer hardware. The lighting fixture may include an LED and/or may be one of a plurality of networked lighting fixtures. The lighting system may further include a mounting apparatus for holding the lighting fixture and/or a surface for the reflection of illumination.

In a still further embodiment there is disclosed a method for allowing a software developer to include control of a lighting system within a software application comprising: providing a lighting system substantially similar to one provided to a user to a software developer; and providing an interface for allowing the lighting system to communicate with a computing device to a software developer; wherein the software developer can use the interface to include control for the lighting system within a software application. There can also be provided a library of prebuilt effects that can be used to generate a particular lighting effect on the lighting system to the software developer.

BRIEF DESCRIPTION OF DRAWINGS

The foregoing and other objects and advantages of the invention will be appreciated more fully from the following further description thereof, with reference to the accompanying drawings, wherein:

FIG. 4 shows an embodiment of speakers with a lighting system built in.

FIG. 9 shows a flow diagram for a method of mapping real world lights and virtual lights to facilitate the coordinated control of lighting with the execution of a computer application.

FIG. 10 shows the schematic of a system for storing files for the coding of an application for control of lighting in coordination with execution of a computer game.

FIG. 11 shows a file structure for a configuration file for a method depicted in connection with FIG. 9.

DETAILED DESCRIPTION OF THE PREFERRED EMBODIMENT(S)

Figure 1:
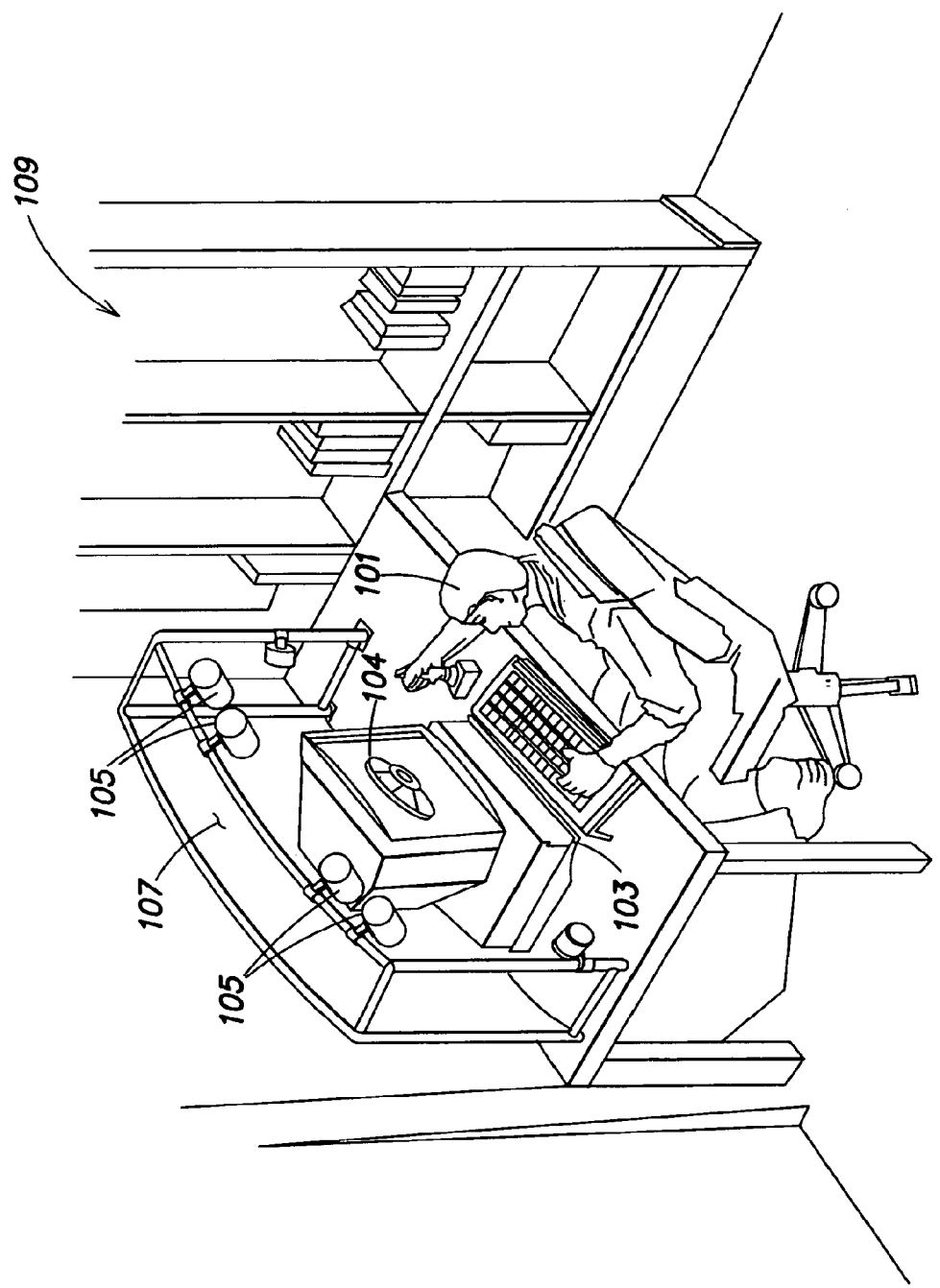
FIG. 1 shows a computer user with an embodiment of a lighting system.

To provide an overall understanding of the invention, certain illustrative embodiments will now be described, including various applications for programmable LED's and LED lighting systems. However, it will be understood by those of ordinary skill in the art that the methods and systems described herein may be suitably adapted to other environments where programmable lighting may be desired, and embodiments described herein may be suitable to non-LED based lighting. The descriptions below focus primarily on using LED lighting systems for enhancement of computer games as that term would be understood by one of skill in the art. In particular, the below embodiments focus primarily on a "first person" type of interactive game involving space battles where the software controlling the game is present on a user's computer, for example installed on the user's hard drive or on a CD ROM or other storage media controlled by the user. One example of such a computer game is produced by Mad Dog software under the title "Star Trek: Armada." This type of computer game represents only one type of computer game with which the below described systems and methods can be used. One of skill in the art would readily see how to apply the below-described embodiments to other types of computer games. Further these games need not be present on the user's computer but could be run off of a network such as, but not limited to, the World Wide Web, the Internet, or any extranet or intranet network, or could be console-type or video-parlor-type computer or video games. In addition, one of skill in the art would understand that the embodiments described below could be used in conjunction with any type of computer software that need not be a game, but of any type of computer application. Further, the user need not be operating a computer, but could be operating any type of computing device, capable of running a software application that is providing that user with information.

In computer games, there is typically a display screen (which could be a personal computer screen, television screen, laptop screen, handheld, gameboy screen, computer monitor, flat screen display, LCD display, PDA screen, or other display) that represents a virtual world of some type. There is also typically a user in a real world environment that surrounds the display screen. The present invention relates to computer games and their surrounding environment.

In an embodiment of the invention described herein, the environment of a user of a computer game includes one or more light systems. As used herein "light systems" should be understood where context is appropriate to comprise all light systems, including LED systems, as well as incandescent sources, including filament lamps, pyro-luminescent sources, such as flames, candle-luminescent sources, such as gas mantles and carbon arc radiation sources, as well as photo-luminescent sources, including gaseous discharges, fluorescent sources, phosphorescence sources, lasers, electro-luminescent sources, such as electro-luminescent lamps, light emitting diodes, and cathode luminescent sources using electronic satiation, as well as miscellaneous luminescent sources including galvano-luminescent sources, crystallo-luminescent sources, kine-luminescent sources, thermo-luminescent sources, triboluminescent sources, sonoluminescent sources, and radioluminescent sources. Light systems may also include luminescent polymers capable of producing primary colors.

As used herein, the term "LED" means any system that is capable of receiving an electrical signal and producing a color of light in response to the signal. Thus, the term "LED" should be understood to include light emitting diodes of all types, light emitting polymers, semiconductor dies that produce light in response to current, organic LEDs, electro-luminescent strips, and other such systems. In an embodiment, an "LED" may refer to a single light emitting diode having multiple semiconductor dies that are individually controlled. It should also be understood that the term "LED" does not restrict the package type of the LED. The term "LED" includes packaged LEDs, non-packaged LEDs, surface mount LEDs, chip on board LEDs and LEDs of all other configurations. The term "LED" also includes LEDs packaged or associated with phosphor wherein the phosphor may convert energy from the LED to a different wavelength. An LED system is one type of illumination source.

The term "illuminate" should be understood to refer to the production of a frequency of radiation by an illumination source. The term "color" should be understood to refer to any frequency of radiation within a spectrum; that is, a "color," as used herein, should be understood to encompass a frequency or combination of frequencies not only of the visible spectrum, including white light, but also frequencies in the infrared and ultraviolet areas of the spectrum, and in other areas of the electromagnetic spectrum.

Figure 5:
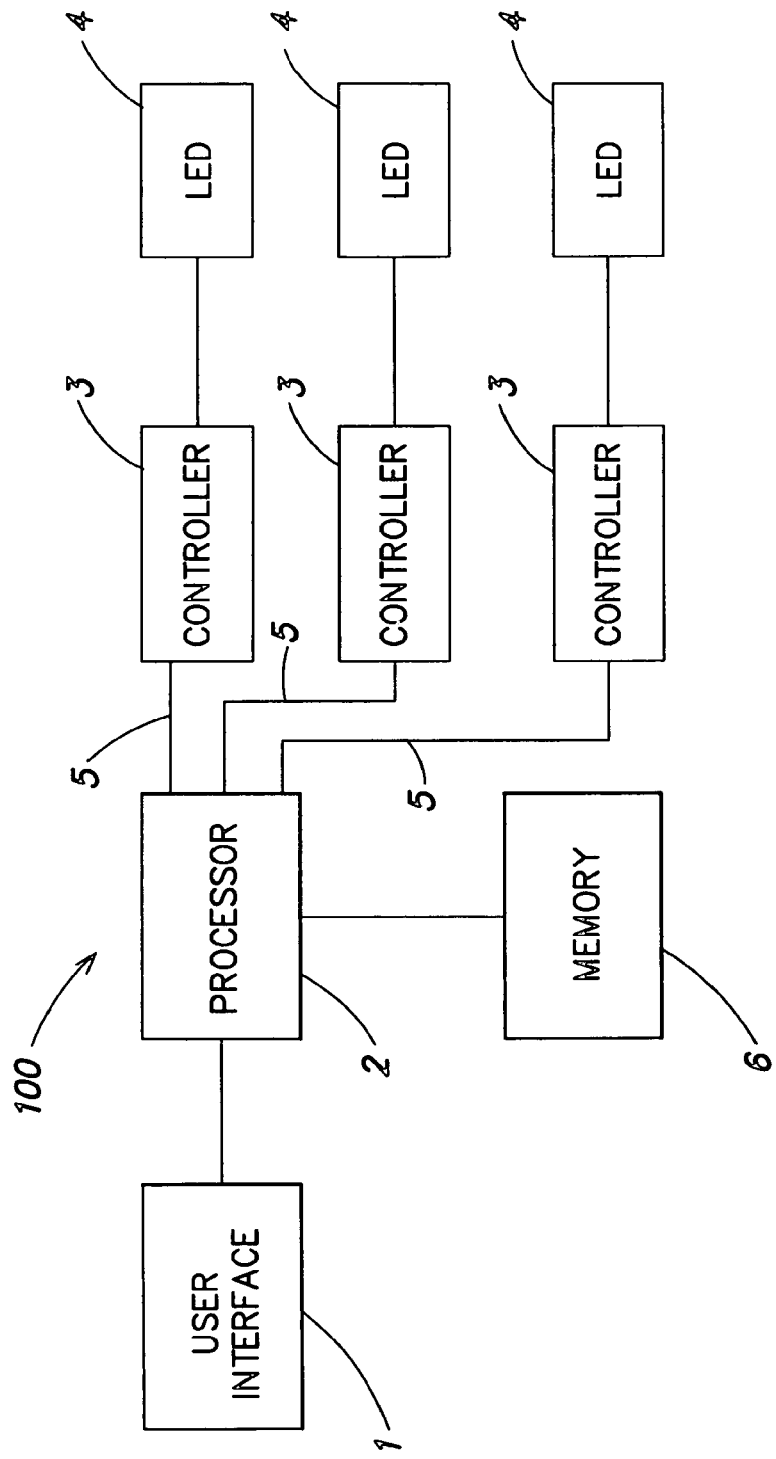
FIG. 5 shows an embodiment of a lighting system which could be used herein.

FIG. 5 illustrates a block diagram of one embodiment of an illumination system 100. A processor 2 is associated with several controllers 3. The controllers 3 control the power to the LEDs 4. As used herein, the term processor may refer to any system for processing electronic signals. A processor may include a microprocessor, microcontroller, programmable digital signal processor, other programmable device, a controller, addressable controller, microprocessor, microcontroller, addressable microprocessor, computer, programmable processor, programmable controller, dedicated processor, dedicated controller, integrated circuit, control circuit or other processor. A processor may also, or instead, include an application specific integrated circuit, a programmable gate array, programmable array logic, a programmable logic device, a digital signal processor, an analog-to-digital converter, a digital-to-analog converter, or any other device that may be configured to process electronic signals. In addition, a processor may include discrete circuitry such as passive or active analog components including resistors, capacitors, inductors, transistors, operational amplifiers, and so forth, as well as discrete digital components such as logic components, shift registers, latches, or any other separately packaged chip or other component for realizing a digital function. Any combination of the above circuits and components, whether packaged discretely, as a chip, as a chipset, or as a die, may be suitably adapted to use as a processor as described herein. It will further be appreciated that the term processor may apply to an integrated system, such as a personal computer, network server, or other system that may operate autonomously or in response to commands to process electronic signals such as those described herein. Where a processor includes a programmable device such as the microprocessor or microcontroller mentioned above, the processor may further include computer executable code that controls operation of the programmable device. In an embodiment, the processor 2 is a Microchip PIC processor 12C672 and the LEDs 4 are red, green and blue.

The controller 3 may be a pulse width modulator, pulse amplitude modulator, pulse displacement modulator, resistor ladder, current source, voltage source, voltage ladder, switch, transistor, voltage controller, or other controller. The controller controls the current, voltage or power through the LED 4. The controller also has a signal input wherein the controller is responsive to a signal received by the signal input. The signal input is associated with the processor such that the processor communicates signals to the signal input and the controller regulates the current, voltage and or power through the LED. In an embodiment, several LEDs with different spectral output may be used. Each of these colors may be driven through separate controllers. The processor and controller may be incorporated into one device. This device may power capabilities to drive several LEDs in a string or it may only be able to support one or a few LEDs directly. The processor and controller may also be separate devices. By controlling the LEDs independently, color mixing can be achieved for the creation of lighting effects. In an embodiment, memory 6 may also be provided. The memory 6 is capable of storing algorithms, tables, or values associated with the control signals. The memory 6 may store programs for controlling the LEDs 4. The memory may be memory, read-only memory, programmable memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, address information, and program output or other intermediate or final results. A program, for example, may store control signals to operate several different colored LEDs 4. A user interface 1 may also be associated with the processor 2. The user interface may be used to select a program from memory, modify a program from memory, modify a program parameter from memory, select an external signal or provide other user interface solutions. Several methods of color mixing and pulse width modulation control are disclosed in U.S. Pat. No. 6,016,038 "Multicolored LED Lighting Method and Apparatus," the entire disclosure of which is incorporated by reference herein. The processor 2 can also be addressable to receive programming signals addressed to it.

There have been significant advances in the control of LEDs. U.S. Patents in the field of LED control include U.S. Pat. Nos. 6,016,038, 6,150,774, and 6,166,496. U.S. patent application Ser. No. 09/716,819 for "Systems and Methods for Generating and Modulating Illumination Conditions" also describes, among other things, systems and controls. The entire disclosure of all these documents is herein incorporated by reference.

In embodiments of the invention, the lighting system may be used to illuminate a real world environment. On such environment is shown in FIG. 1. In FIG. 1 a user (101) is using a computing device (103). The computing device has a visual display (104). The user also has at least one lighting fixture (105) mounted nearby. Generally the lighting fixtures (105) will be mounted in a manner that the user (101) can see either the illumination projected by a lighting fixture (105) directly, or indirectly, such as by bouncing the illumination off a surface (107). The lighting fixtures in combination comprise the lighting system. The lighting system may be in communication with the computing device (103) by any manner known to one of skill in the art which can include, but is not limited to: wired connections, cable connections, infrared (IR) connections, radio frequency (RF) connections, any other type of connection, or any combination of the above. In an embodiment, control may be passed to the lighting system via a video-to-DMX device, which provides a simple way of generating the lighting signal. Such a device may have a video-in port and a pass-through video-out port. The device may also have a lighting signal port where the DMX, or other protocol data, is communicated to the lights in the room. The device may apply an algorithm to the received video signal (e.g. average, average of a given section or time period, max, min) and then generate a lighting signal corresponding to the algorithm output. For example, the device may average the signal over the period of one second with a resultant value equal to blue light. The device may then generate blue light signals and communicate them to the lighting system. In an embodiment, a simple system would communicate the same averaged signal to all of the lights in the room, but a variant would be to communicate the average of a portion of the signal to one portion of the room. There are many ways of partitioning the video signal, and algorithms could be applied to the various sections of the light system, thus providing different inputs based on the same video signal.

In the depicted embodiment the surface (107) comprises a screen designed to reflect light. Alternatively the surface could be, but is not limited to, a wall or other surface upon which light could be reflected. In another embodiment, the surface could be designed to absorb and retransmit light, possibly at a different frequency. For instance the surface (107) could be a screen coated with a phosphor where illumination of a particular color could be projected on the screen and the screen could convert the color of the illumination and provide a different color of illumination to the user (101). For instance the projected illumination could primarily be in the blue, violet or ultraviolet range while the transmitted light is more of a white.

In an embodiment, the lighting system is placed in a real world environment (109) that includes the computing device (103) and the user (101). The real world environment (109) could be a room that includes a computer. The lighting system could be arranged, for example, to light the walls, ceiling, floor or other sections or objects in a room instead of, or in addition to lighting the surface (107). The lighting system may include several addressable lighting systems with individual addresses. With this system, much like the surface (107), the illumination can be projected so as to be visible to the user (101) either directly or indirectly. That is a lighting fixture (105) could shine so that the light is projected to the user without reflection, or could be reflected, refracted, absorbed and reemitted, or in any other manner indirectly presented to the user (101).

Figure 7:
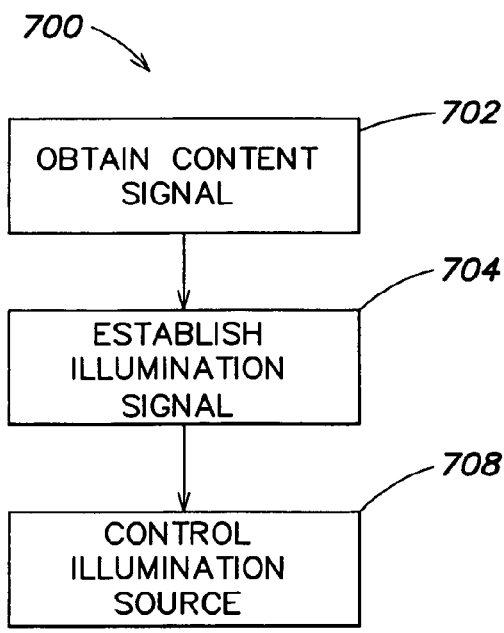
FIG. 7 shows a flow diagram for a method of coordinating illumination of an environment with execution of content of a computer application.

Referring to FIG. 7, a flow diagram 700 depicts basic steps for providing for coordinated illumination of an environment in conjunction with execution of a computer application such as a game. At a step 702, the provider of the system provides for obtaining a content signal 702 that relates to content from the computer game. For example, the content signal may be computer code for execution of the computer game, or a video or other signal that comes from the computer game system for display on a television or a monitor. At a step 704 the host establishes a system for controlling illumination of a real world environment, such as installing lights in a desired configuration, such as an array of color LEDs located in the area of the user and positioned to illuminate the surface 107 of FIG. 1. The system further includes a processor or other element for allowing the host to change illumination. Next, at a step 708, the user coordinates the illumination control with the nature of the content signal obtained at the step 702. For example, upon receiving certain code or a certain signal from the computer game system, the illumination system may be controlled to change the illumination in the environment. Further detail will be provided in connection with the embodiments described below.

The surface (107) may also include one or more colors, figures, lines, designs, figures, pictures, photographs, textures, shapes or other visual or graphical elements that can be illuminated by the lighting system. The elements on the surface can be created by textures, materials, coatings, painting, dyes, pigments, coverings, fabrics, or other methods or mechanisms for rendering graphical or visual effects. In embodiments, changing in the illumination from the lighting system may create visual effects. For example, a picture on the surface (107) may fade or disappear, or become more apparent or reappear, based on the color of the light from the lighting system that is rendered on the surface (107). Thus, effects can be created on the surface (107) not only by shining light on a plain surface, but also through the interaction of light with the visual or graphical elements on the surface.

In use, the illumination system can be used to provide information to the user (101) in response to or in coordination with the information being provided to the user (101) by the video display (104). One example of how this can be provided is in conjunction with the user playing a computer game on the computing device (103). The light system may be used to create one or more light effects in response to action on the video display (104). The lighting effects, or illumination effects, can produce a vast variety of effects including color-changing effects; stroboscopic effects; flashing effects; coordinated lighting effects; lighting effects coordinated with other media such as video or audio; color wash where the color changes in hue, saturation or intensity over a period of time; creating an ambient color; color fading; effects that simulate movement such as a color chasing rainbow, a flare streaking across a room, a sun rising, a plume from an explosion, other moving effects; and many other effects. The effects that can be generated are nearly limitless. Light and color continually surround the user, and controlling or changing the illumination or color in a space can change emotions, create atmosphere, provide enhancement of a material or object, or create other pleasing and or useful effects.

It is important to note that the lighting system producing illumination in response to the information provided on the screen allows the lighting system to describe or indicate activity that is not represented on the screen in any way. The best example of this is by thinking of the user (101) using the video display (104) as a viewport into a virtual environment created by the computing device (103). In the virtual environment, something could be behind the user, however, the video display may only show a view in front of the user. The user could "turn around" and see the object behind them by rotating the viewport. Objects which are behind the user in this virtual environment could still be objects which a user in a real environment would be able to see because their vision is not limited by a viewport into the real environment. The view through the viewport, however defines a particular positioning within the virtual world (a placement and a facing). Therefore, the lighting system could show or indicate information about what is behind the user. This information is still produced in coordination with what is produced on the video display because the particular video display defines the user's location in the virtual world. The lighting system therefore provides information in coordination with or in response to the video display that is not actually pictured on the video display. In particular, it provides information that there is something not currently in view of the viewport of the visual display, but present in the virtual world.

In one embodiment, the lighting system may be used to extend the area of the user's (101) vision beyond the edges of the video display. Referring to FIG. 1, the user could be playing a game where the user is at the controls of a starship and there are various objects in a surrounding virtual space. The video display could show the view out of the supposed front of the starship showing other starships, planets, or other cosmic phenomena visible out the front of the starship. In many games, however, the world is not defined solely by what is in front of the starship but the user is supposed to have a first person view into a world that surrounds them. For instance another starship could be behind the starship the user is piloting in the game. The illumination system could provide indications as to locations of other objects beyond the visual display. For example, a starship may be displayed on the video display and the starship may appear to be irradiated with a blue light. The blue light may be coming from a light source within the game environment, possibly a nebula that is outside the viewing parameters of the screen of the video display. The nebula may be outside the upper right hand corner of the screen for instance. The lighting system could be used to create a light source visible to the user at the appropriate location based on the apparent irradiation on the ship. In FIG. 1 this may be accomplished by having a blue light reflect off surface (107) at the point appropriate for the nebula.

The illumination can be used to extend beyond the boundaries of the video display or the user's actual vision. For instance, in the game world the user's starship may be being attacked from behind. The illumination system could pass on this information to the user by flashing lights behind the user with a red color indicating to the user that they are being attacked from the rear. The user sees the illumination as it passes over the user and reflects off of the surface or other objects surrounding the user. In this case, while there may be no indication of the rear attack on the video display, the lighting system provides the information to the user.

The example of a rear attack shows that a surface (107) may be replaced or augmented by light in the entire user's environment, or by other surfaces. The entire room or environment in which the user is playing could be used to extend the effective viewing space of a computer monitor. For example, a flash of light representing an explosion could be generated behind a user to create the feeling that the explosion actually occurred behind the user. This could also be coordinated with sound such that the sound and light appear to be coming from the same area of the room. Such activity can allow for a more in-depth game playing environment. As discussed above the user in the game may be supposed to have a "first person" view into the game world. By surrounding the user with illumination, the user may be able to have real world space provide a simulation of that world outside the display on the video display. Further a moving object could appear to leave the video display and continue moving. For instance, the light from an explosion could begin on the video display, and appear to race toward and even through the user.

Figure 2:
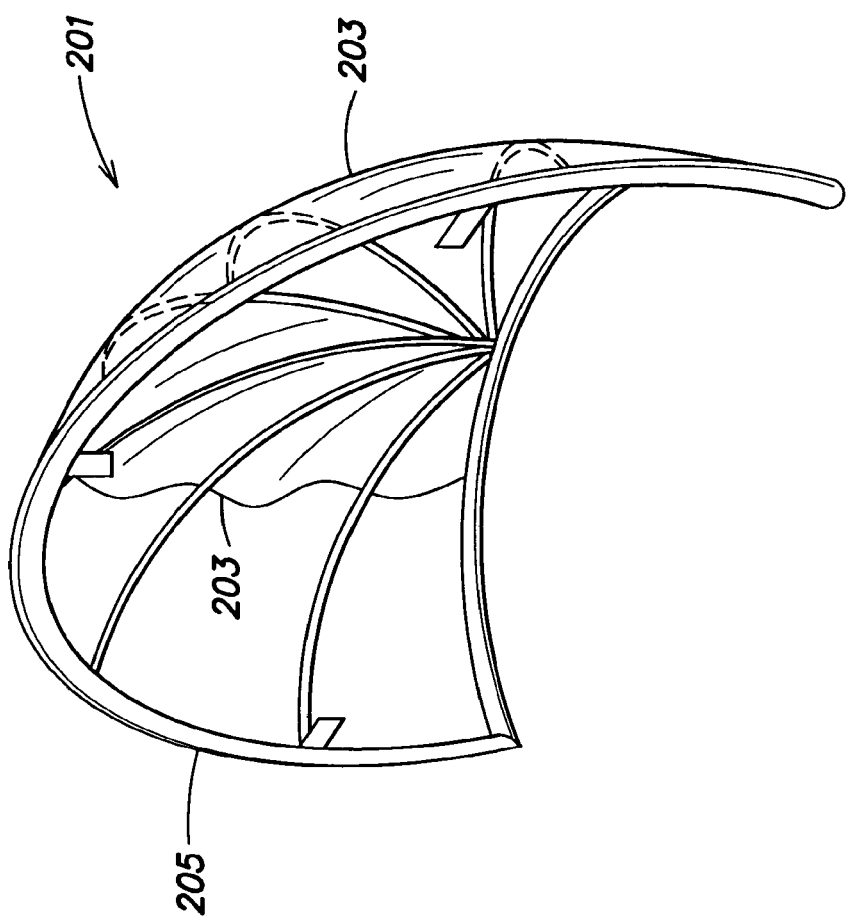
FIG. 2 shows an embodiment of a cabana for use with a lighting system.

As discussed above, the lighting system may make use of a surface or screen to provide a location of the user's viewing of the projected illumination. A screen may be useful because it can provide a set real world environment designed to allow easy control over the illumination outside the video display. In embodiments of this invention, there is a screen unit that is associated with the computer and that is used to reflect color output from the light system. In an embodiment, the screen unit is an enclosure such as a cabana that is used to surround the display screen of a computer, wherein the cabana reflects back color from color lights. One embodiment of such a cabana is shown in FIG. 2. The cabana in FIG. 2 includes a frame 201 supporting fabric 203 in a rigid or semi rigid structure such as a miniature tent. The fabric could be selected to provide a high reflectivity and good visualization of light. Further, the cabana having a quarter spherical shape, or other three-dimensional shape, can allow distance to be portrayed without use of imposed perspective. Such a design may also allow for the placement of the surface over a standard video display. The cabana in FIG. 2 also includes a mounting bar (205) upon which lighting fixtures may be mounted either temporarily or permanently. The advantage of such a mounting bar is that the cabana could be assembled and disassembled and the lighting fixtures could be very quickly aimed to the appropriate points on the fabric (203) even if the assembler did not know the appropriate aiming of the lights. In one embodiment, clips or other mounting devices can be included on mounting bar (205) that only allow a particular installation of a particular fixture aimed in a particular direction. Other examples of screens and enclosures for reflecting light from the light system are set forth in appendix A. The enclosures could be anything from small, collapsible units, to large, even building-sized, arrangements. Any enclosure designed to be associated with a display screen for a computer game and to reflect color light from a light system associated with the computer game should be understood to be encompassed by the present disclosure. In an embodiment of the invention, there may be a light screen permanently associated with a computer for reflecting light that represents an attribute of an object of a program running on the computer. The screen could be a completely or partially enclose an environment, such as computer surrounded by an enclosure of white or other material. One example could be a completely enclosing arcade game setup as is known to the art. Any number of lights (lighting fixtures) may be used to light the screen. The one or more lights may include several addressable lighting systems and the projected illumination from individual lighting fixtures may be distinct, overlapped, or both on the screen. The screen itself could also contain lighting fixtures not aimed at the screen; for instance, lighting fixtures could be placed on mounting bar (205) and aimed at the user.

Figure 3:
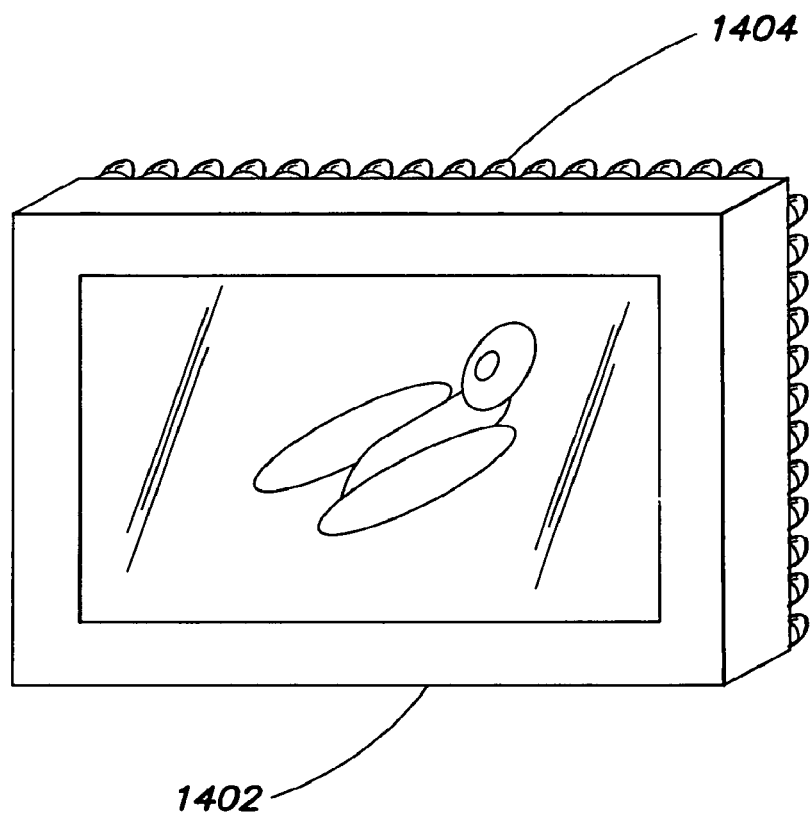
FIG. 3 shows an embodiment of a video display with a lighting system built in for displaying illumination indirectly to a user.

There are many ways that the lighting fixtures can be arranged and lighting systems can be generated to illuminate a surface or shine directly on the user. FIG. 3 illustrates an embodiment where the lighting system (1404) is incorporated onto a housing for the video display (1402). This device can be used in place of a more complicated layout of lighting units, or it can be used in conjunction with the other lighting units. The lighting system (1404) can be divided up into several sections to provide stereo or other multi-channel lighting effects around the video display. For example, the lighting system (1404) can be divided into three segments, right side, left side and top. A light track could contain light control information for each of these sections such that light of any color can be emitted from any side of the video display (1402). This may be useful in extending the effects from the video display (1402) onto a wall or screen behind it. For example, if the right side of the video display is blue the lighting on that side of the video display (1402) could also light the wall blue. Flashes of lightning that cover the entire screen could be flashed all around the video display (1402). If an automobile's headlights start on the right side of the screen and move to the left, the lighting system (1404) could follow the same pattern.

Figure 4:
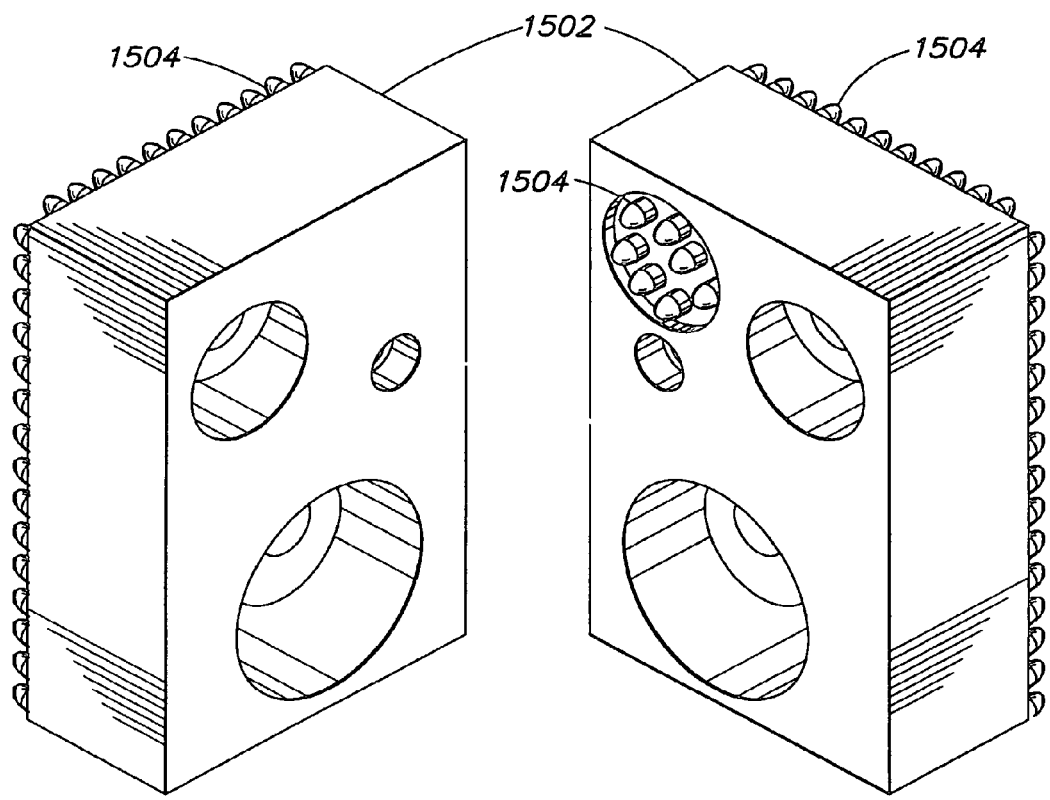

FIG. 4 illustrates an embodiment where the lighting system (1504) is incorporated with the speaker (1502) of a sound system. This device can be used in place of a more complicated layout of lighting units or it can be used in conjunction with the other lighting units. The lighting unit (1504) can also be divided up into sections although a large benefit from this embodiment is to use it as a single lighting element to project the light in various sections of the room where the user had already placed speakers. Therefore setup of a surround sound system, as would be understood by one of skill in the art, could also allow for the setup of a surround light system at the same time. The benefits of this are apparent. For example, the sound of an explosion traveling over the user via the speaker can be complemented by the light of the explosion traveling in the same manner.

The examples discussed above primarily relate to systems where a real world light system in the user's environment can generate light output that reflects, indicates, or is associated with objects or events in the virtual environment of a computer game. Conversely, the virtual environment can reflect events in the real world environment, such as when the lights are coupled with sensors, receivers, or other inputs for receiving data. For instance, a sensor could detect that the light from a particular fixture is being blocked, indicating the user has stood up and is taking a break from the game and the fixtures should be powered down to save energy, and the user's game should be paused. A wide range of detected conditions could be used to provide input or feedback to the game and should be understood to be encompassed herein, for example detection of the presence of absence of the user in room or in proximity to the display screen, biometric characteristics of the user, such as heart rate, blood pressure, body temperature or the like, room lighting, temperature, and sound levels, and many others. In embodiments the detected conditions can be used to influence the game. For example, if a user's pulse reached a certain level, the game could alter play to provide a less (or more) stressful set of events.

In embodiments, the light system may be associated with code for the computer game, so that the computer game code is modified or created to control the light system. For example, object-oriented programming techniques can be used to attach attributes to objects in the computer game, and the attributes can be used to govern behavior of the real world light system. Object oriented techniques are known in the field, and can be found in texts such as "Introduction to Object-Oriented Programming" by Timothy Budd, the entire disclosure of which is herein incorporated by reference. It should be understood that other programming techniques may also be used to direct lighting systems to illuminate in coordination with games, object oriented programming being one of a variety of programming techniques that would be understood by one of ordinary skill in the art to facilitate the methods and systems described herein.

In an embodiment, a developer can attach the light system inputs to objects in the game. For example, the developer may have an abstraction of a light that is added to the code construction, or object, of a game object. An object may consist of various attributes, such as position, velocity, color, intensity, or other values. A developer can add light as an instance in the object in the code of a game. For example, the game object could be a ship, with attributes, such as position, size, velocity, etc. A light source can be added as an instance of the object of the game, and the light source can have attributes, such as intensity, color, and various effects. Thus, when events occur in the game that call on the object of the ship, a thread running through the program can draw code to serve as an input to the processor of the light system. The light can accurately represent geometry, placement, spatial location, represent a value of the attribute or trait, or provide indication of other elements or objects.

Figure 8:
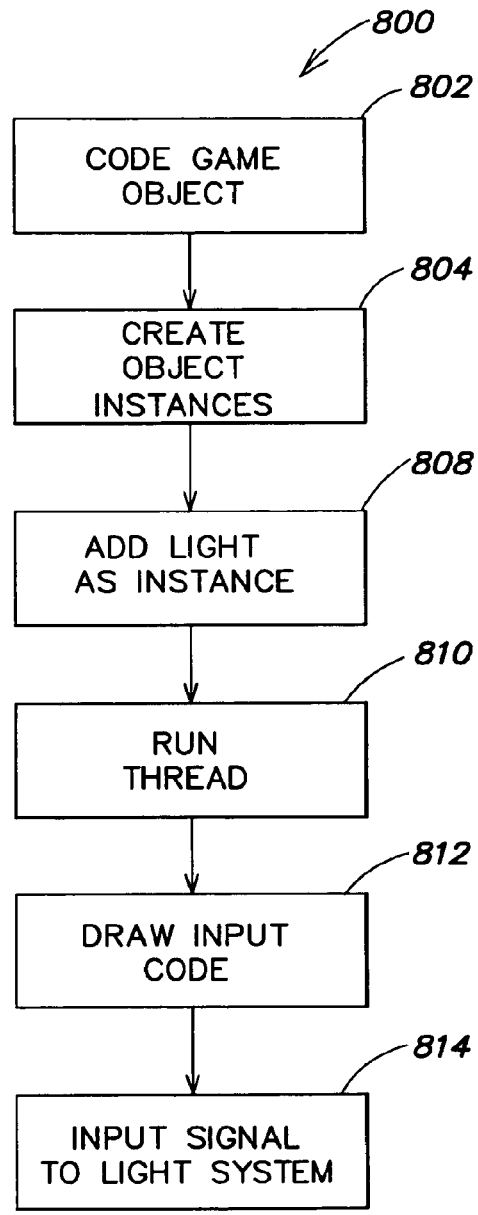
FIG. 8 shows a flow diagram for a method of adding lighting as an instance of an object-oriented programming technique used to code a computer game.

Referring to FIG. 8, a flow chart 800 provides steps for a method of providing for coordinated illumination. At the step 802, the programmer codes a game object for a computer game, using, for example, object-oriented programming techniques. At a step 804, the programming creates instances for each of the objects in the game. At a step 808, the programmer adds light as an instance to one or more objects of the game. At a step 810, the programmer provides for a thread, running through the game code. At a step 812, the programmer provides for the thread to draw lighting system input code from the objects that have light as an instance. At a step 814, the input signal drawn from the thread at the step 812 is provided to the lighting control system, so that the lighting system responds to code drawn from the computer game.

Using such object-oriented light input to the light system from code for a computer game, various lighting effects can be associated in the real world with the virtual world objects of a computer game. For example, in a space battle game, a ship's light source can be attached with an effect, such as sound, flashing, motion, vibration and other temporal effects. Further, the light system could include other effects devices including sound producing devices, motion producing devices, fog machines, rain machines or other devices which could also produce indications related to that object.

Referring to FIG. 9, a flow diagram 900 depicts steps for coordinated illumination. In embodiments, the program code for the light has a separate thread running on the machine. At a step 902 the program initiates the thread. At a step 904 the thread as often as possible runs through the list of virtual lights. At a step 908 the thread does three-dimensional math to determine which real-world lights are in proximity to reference point in the real world (e.g., the head of the user) that is projected as the reference point of the coordinate system of objects in the game. Thus, the (0,0,0) position can be the user's head in the real world and a point on the screen in the game (for instance the center of the video display and therefore the user's view into the virtual environment). At a step 910, the code maps the virtual environment and object in it to the real world environment, including the light system, so that events happening outside the computer screen are similar in relation to the reference point as are virtual objects to a reference point on the screen. At a step 912, the host may provide an interface for mapping. The mapping function may be done with a function, e.g., "project-all-lights," as described in Directlight API described below and in Appendix A, that maps real world lights using a simple user interface, such as drag and drop interface. The placement of the lights may not be as important as the surface the lights are directed towards. It may be this surface that reflects the illumination or lights back to the user and as a result it may be this surface that is the most important for the mapping program. The mapping program may map these surfaces rather than the light fixture locations or it may also map both the locations of the fixtures and the light on the surface. In one embodiment a screen, such as the cabana discussed above, can further simplify this mapping by providing a set and unchanging lighting system and screen that will have identical properties no matter the real world environment in which the system is located.

A system for providing the code for coordinated illumination is depicted in FIG. 10, which may be any suitable computer capable of allowing programming, including a processor 1002, an operating system 1004, and memory, such as a database 1008, for storing files for execution.

Each real light may have attributes that are stored in a configuration file. An example of a structure for a configuration file 1100 is depicted in FIG. 11. The configuration file 1100 may include various data, such as a light number 1102, a position of each light 1104, the position or direction of light output 1108, the gamma (brightness) of the light 1110, an indicator number for one or more attributes 1112-1114, and various other attributes. By changing the coordinates in the configuration file, the real world lights can be mapped to the virtual world in a way that allows them to reflect what is happening in the virtual environment. The developer can thus create time-based effects, such as an explosion. There can then be a library of effects in the code that can be attached to various game attributes. Examples include explosions, fades in and out, etc. The developer attaches the effects to virtual lights in the game. For example, when an explosion is done, the light goes off in the game, reflecting the destruction of the object that is associated with the light in the configuration file.

Figure 12:
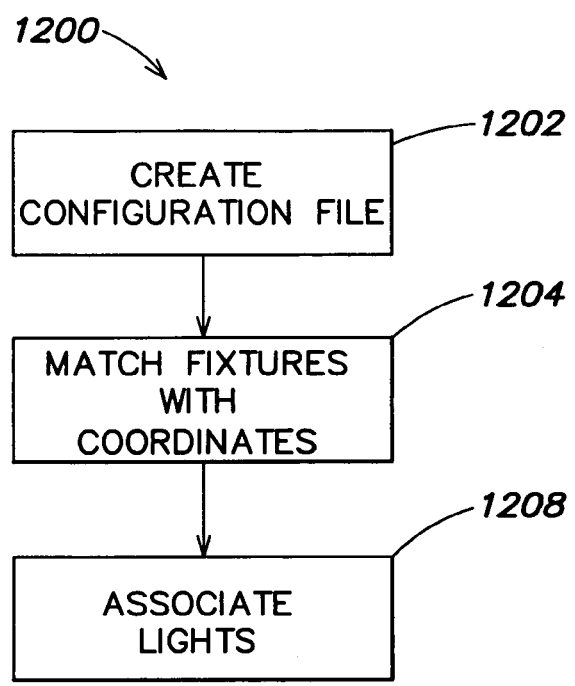
FIG. 12 shows a flow diagram for creation and use of a configuration file for coordinated illumination.

To simplify the configuration file, various techniques can be used. In embodiments, hemispherical cameras, sequenced in turn, can be used as a baseline with scaling factors to triangulate the lights and automatically generate a configuration file without ever having to measure where the lights are. Referring to the flow diagram 1200 of FIG. 12, in embodiments, the configuration file is created at a step 1202. The configuration file can be typed in, or can be put into a graphical user interface that can be used to drag and drop light sources onto a representation of a room. At a step 1204, the developer can create a configuration file that matches the fixtures with true placement relative to a user's coordinate in the real room. For example, once the lighting elements are dragged and dropped in the environment, at a step 1208 the program can associate the virtual lights in the program with the real lights in the environment. An example of a light authoring program to aid in the configuration of lighting is included in U.S. patent application Ser. No. 09/616,214 "Systems and Methods for Authoring Lighting Sequences." Color Kinetics Inc. also offers a suitable authoring and configuration program called "ColorPlay."

Further details as to the implementation of the code can be found in the Directlight API document attached hereto as Appendix A. Directlight API is a programmer's interface that allows a programmer to incorporate lighting effects into a program. Directlight API is attached in Appendix A and the disclosure incorporated by reference herein. Object oriented programming is just one example of a programming technique used to incorporate lighting effects. Lighting effects could be incorporated into any programming language or method of programming. In object oriented programming, the programmer is often simulating a 3D space in the screens. The 3D space continues throughout the room the gamer is in and beyond to virtual infinity. In this 3D space, the programmer may place an object, such as a starship, as well as a virtual light, such as a nebula, sun, star, other star ship, photon beam, weapon, explosion plume or other light generating object.

In the above examples, lights were used to indicate the position of objects which produce the expected light or have light attached to them. There are many other ways in which light can be used. The lights in the light system can be used for a variety of purposes, such as to indicate events in the game, to indicate levels or attributes of game objects, such as characters, ships, weapons, shields, health, playing pieces, environments, rooms, or other objects. For instance the lights could turn to a particular color (for instance green) representing the shield strength of a starship. As the shields were slowly knocked down by enemy fire, the lights could change color or slowly fade out indicating the shield strength is fading. The lights can be used for aesthetic purposes, such as to connote a mood for an object or an environment in the game. For instance, the lights could change color to indicate the passage of time in the game world, or could produce lighting effects to simulate environment effects. For instance the lights could have an appropriate flicker to indicate that it is raining in the game world. A wide range of effects can be used, each associated with a particular object or event in the game. The lighting system could provide further indications such as by triggering a real world fog machine, when the virtual environment is supposed to be foggy.

In embodiments, there may be an be an optional override mechanism that takes over one or more lights and direct them to do something regardless of what the virtual light source is intended to do. This may be useful when the program requires all of the lights in the system to change to a particular color. For example, the game may be played out in a space environment where the starship is lighted blue from a nearby nebula, when suddenly the ship is attacked by another ship. The program can instantly change all of the lights in the system to flashing red to indicate a red alert. The pulsation of the lights may be coordinated with the sound of an alarm or other sensations to further immerse the user.

In embodiments, an object, such as a ship's light source, can be associated with lights outside the game or any purposeful lighting setup, such as room lights. Any real world lighting fixture could be used as part of a lighting system as discussed herein Optionally, direct access to outside lights can override the light source in the game. For example, the video display can provide user interface information, such as red alerts, strength of a unit or other attributes of game objects through the lights. In effect the video display could be disabled and only lights could be used. Such an embodiment could enable a computer game to be created which uses the lights as the sole source of information, or alternatively, the video display device could be disabled to indicate a particular situation has occurred. Returning to the starship example, a situation could occur where the starship has been "blinded" as part of the game actions. This may result in the forward view being unavailable to the user. However, the user can still navigate the starship using the lighting system. This ability can add a depth of play that has previously been unavailable to a computer game because the screen video display has previously been the only that provides visual feedback.

It is also possible to have light system lights that are not attached to objects in the game, such as to indicate another environmental condition, such as the end of the work day, sunset, sunrise, or some other indicator that is useful to a player immersed in the game. The may also provide mood or aesthetics such as projecting the presence of a person, creature object, or other thing such as by an aura or their traits of good and evil. These traits could be associated with colors and intensities. Approaching a dangerous object could also have the lights switch to a warning mode (such as flashing red) to warn the user of the danger.

In yet another embodiment, the lights could act as a detriment to game play to show various conditions. For instance, in certain computer games the user is supposed to be hampered because they have carried out a particular action in the game. For instance the sound may be cut off because the user was to close to a virtual explosion and they were "deafened" by it. Such feedback is common, often with the user's video display acquiring random noise or color to disorient the user. One example of how lights could be used if a player was too close to an explosion, the lights could provide for blinking "spots" to distract the user and degrade their game play. Alternatively, if the game universe indicated the user was supposed to be drunk, disoriented, or otherwise distracted, the lights could flash or change color is disorienting patterns to actually distract the user from their game play.

In the embodiments above, a system is primarily discussed where the computer code is designed to interact with a three-dimensional virtual world of which the user is part. The code works well to translate from the three dimensional objects into the real three-dimensional world. To hook up the lights to a two-dimensional world, additional programming may be required and additional conditions may need to be put into effect. In a two-dimensional world, the code is not necessarily designed to place the real world user at a reference point, so the code may need to adapt to place the real world user in the environment in the same position as the virtual "user" (called a character) in the game. Alternatively, it may be undesirable to control the lighting systems illumination to indicate what the user's character is seeing in the virtual world. Instead, the lighting system may extend the world the user sees. One example of a 2-D game is "Diablo" produced by Blizzard software. In this game the user looks down on a map which contains a representation of the character the user is controlling. As opposed to the first person view discussed above, in this game the user has a third person view looking down on the character that is supposed to be them. The screen then provides a perspective layout of a game world of which the character is a part. If the illumination system provides the view as the character would see it, the user may be confused (for instance a fire could be burning at the lower right corner of the screen but be represented by a lighting fixture behind and to the left of the user, based on the facing of the character, the character could then turn in place resulting in minimal change of the information on screen, but a dramatic shift in the illumination produced by the lighting system. It may therefore be desirable to extend any perspective or view of a 2-D game in a manner so that the lighting system illuminates in a manner to conform with the view on the video display. Following with the above example the lights may track to follow the fire off screen as the character moves away from the fire. This could occur by defining a "plane of the game" representing the game world as if the user was not present at all and only the character existed. Therefore as the character in the game moved up and left from the fire, the fire appears to move, via the lighting system, down and to the right.

In one embodiment of the invention, the lighting system can be replaced or augmented by lights already present in the real world environment. For instance, one can create a game that involves the use of the lights in the house. One can use the game itself as a user interface for the lights in the house. A good example might be a horror game where when the lights go out in the game environment, they also go out in the real world room. Such an environment could be highly engaging to a user who is placed even more within the virtual world in which they are playing by having that world truly interact with the real world where they are.

Figure 13:
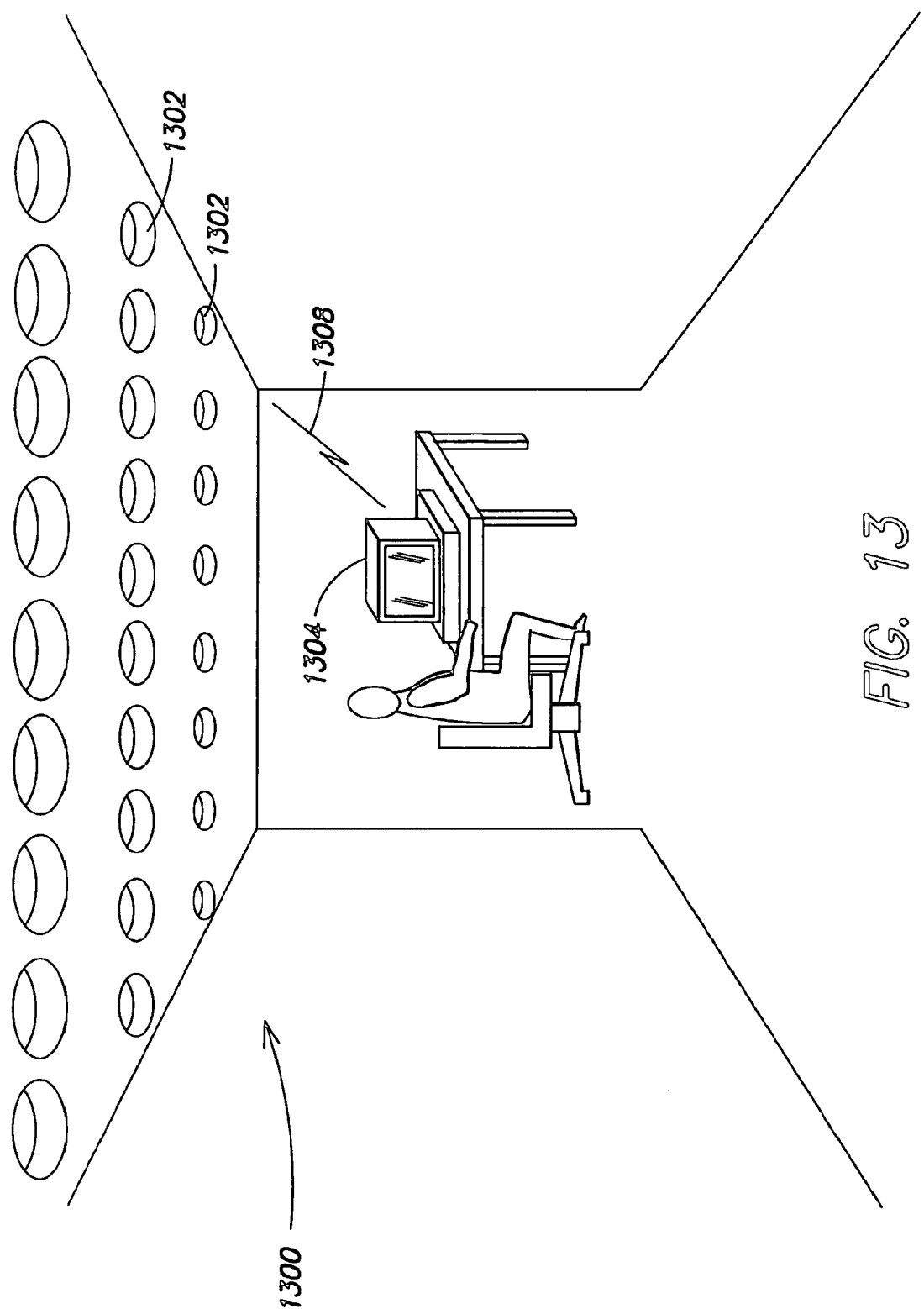
FIG. 13 shows an embodiment of coordinated illumination wherein a portion of a real world environment is lit by an array of light emitting diodes.

The real lights in the house could be made game objects for the game itself, or particular light arrangements could be created for the purposes of playing particular games. Referring to FIG. 13, a system 1300 for using an array of lights 1302 in conjunction with a computer system 1304 (which can be any conventional computer system that provides a connection 1308 to the lights 1302. The array 1302 can be disposed on a wall or the ceiling, as depicted in FIG. 13. The individual LEDs or other lights in the array 1302 can be provided with changes in on-off status, color, and intensity, serving in effect like pixels on display. Thus, a version of a game such as "pong" or other simple game can be played with an array of lights in the light system, with the lights in the array serving as "pixels" analogous to the virtual environment on the screen. In such embodiments it may be unnecessary to use the screen of the computer system 1304 to play the computer game. Alternatively, one player could use the screen to control the game being played, while other players are totally immersed in a gaming environment. As discussed above, a player could be playing a horror game while the players in the next room are experiencing the light sensations from his play without control over the game environment. Essentially they can experience the game play as a third party along for the ride in the game. Further the layout of lights in a house could denote the parameters for a particular game. For instance, a game could be created where the user is fighting off evil monsters in their own home and the lighting in their home is acting in the same manner as the lighting in the game. Such a game environment could be creating by receiving information about the location of lights in a house, and generating the game world to conform to that lighting.

Figure 14:
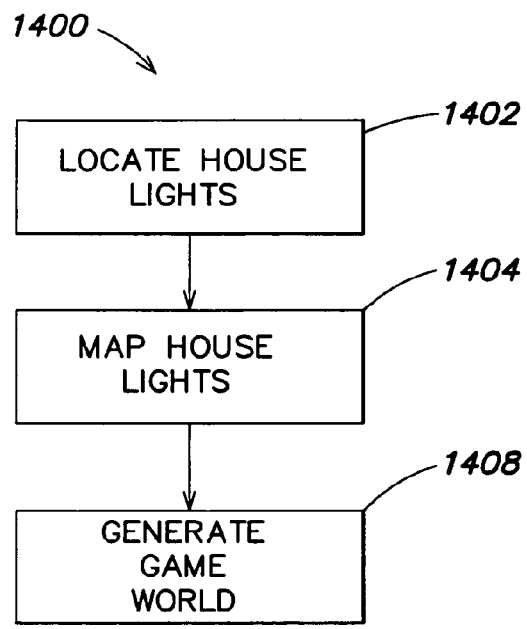
FIG. 14 shows a flow diagram for mapping of house lights to lights in a virtual lighting environment.

FIG. 14 depicts a flow chart 1400 with steps for programming a system to coordinate house lights with a game. At a step 1402 the programmer locates the real-world location of each of the house lights. At a step 1404 the programmer maps the lights, such as by dragging and dropping representations of the locations of the lights onto a virtual representation of the house on the display screen of the computer. At a step 1408 the program generates a game world that contains virtual lights that match the lights of the real world. Then, changes in the game lights can change the room lights, such as in hue or intensity.

It would be easily understood by one of skill in the art that this multi-party experience could be extended to multi-party competitive games such as those commonly played across networks. It could be the case where a user is actually trying to affect the real world environment in which another user is playing. For instance, in the game a first user could be trying to disable an opponent's ship by knocking out its ability to perceive the world around it. For instance it could knock out the ship's forward or rear views. In the real world a second player could actually have various views knocked out (lights being disabled) as the first player accomplishes his goal. In an even more realistic example, the first user could be trying to turn the lights out on the second user. The first person may also directly affect the other person's room lights by, for example, turning the lights off or changing their color, or the first person may indirectly change the lighting conditions in the other persons room by, for example, getting close to the other persons virtual room and tripping a sensor. The first person may also be carrying an object that generates light or reflects light. This object may trigger the lighting in the other person's room to indicate or warn the other person of the first persons presence.

An embodiment may also be an indicator light. A problem with gaming systems and other computer systems in general is the lack of space on a video display. There is only a limited number or amount of dials, indicators, or other status checks that can be placed while still providing a user with a reasonable play environment. A gaming program, for example, may generate an indicator on the video display to indicate a parameter such as the health of the ship, the fuel remaining, the strength of the shields or other parameters. This information is important to the user; however, the indicator takes up valuable video screen, leaving the actual game play area a diminished space and possibly cutting off important user views. An embodiment of the invention may be an indicator light or set of lights that sits on top of the computer screen, for example.

Figure 6:
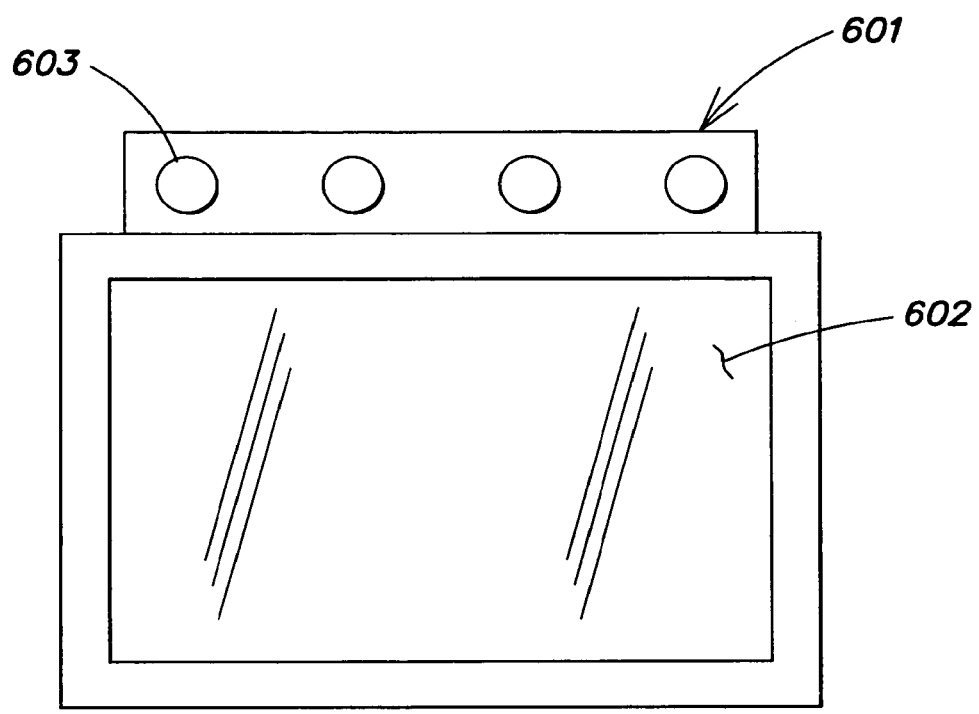
FIG. 6 shows an embodiment of a video display with a lighting system built in for displaying illumination directly to a user.

FIG. 6 depicts a computer screen 602 which could be useful to provide such indicators. An information system 601 may be associated with the computer screen 602. The information system 601 may contain lighting elements 603. In an embodiment, the lighting elements 603 may be aligned as separate lights that can turn on and off and or change in hue, saturation or intensity. For example, the information system may have several independently controllable LED systems and these systems could be controlled in such a manner as to change color to indicate information. For instance, the information could be communicated to the information system through gaming software to indicate the health of an object or person, indicate shield strength, indicate fuel level or any other information that may be useful for the user. In an embodiment, the information system may take the form of a single light source indicating one or more parameters.

The indicators could perform a wide variety of functions including turning on and off, changing color, changing intensity and or other functions to replace or additively improve upon the output from the indicators. For instance, a user's health in the game could be displayed by a number in the corner of the user's screen but could also be represented by a light that changes from green to red as the virtual health drops and flashes insistently when the user's virtual health is perilously low.

In another embodiment, a shield could start as white and fade to another color as it loses strength. The user could start to see "holes" in a shield that are shown by different colors in the room in the direction where the shield is weak allowing a user to quickly realize how to turn to bring more powerful shields to face an enemy. You could see also see a jump into "warp" speed where the front of the room turns bright and then the bright light flashes towards the back of the room, for example. In a racing game, speed could also be simulated as streetlights on screen race down a row of lights off to one side of the user.

In an embodiment, a lit enclosure for the device on which the game is being played changes as an indicator. Game console buttons could also blink to indicate a combination. Like a color-note organ (such as described below), this embodiment could be used in training mode to teach combinations.

Although the figures and description above show primarily computer games, it would be clear to one of skill in the art to carry the system into other types of computing devices and environments. A computing device can include, but is not limited to, any type of computer, a console game system (such as the Playstation series manufactured by Sony), a Personal Digital Assistant (PDA), a telephone, a WebTV or similar system, a thin client, or any other type of system on which a user is able to carry out applications where a lighting system could enhance the display provided to the user. There can be systems where the lighting system provides the only source of visual information to the user.

For console game systems, one of skill in the art would understand that libraries customized onto the proprietary chipsets for console games that drive light system output, similar to the Directlight programmer's interface, could be created without undue experimentation. Console games generally have proprietary chipsets so it may be necessary to generate custom libraries for these systems. The systems and libraries for the consoles could function in much the same way as a PC-based game. The console may include a USB, serial, parallel, firewire, optical, modem or other communications port to communicate with the lighting system. The lighting information could also be sent through a controller port. A controller port may be used for a controller communication as well as lighting control information. Separate controller ports could also be used. For example, a first controller port may be used to communicate with a controller and another controller port may be used to communicate with the lighting system.

Many games and computer systems include input devices such as a joystick, mouse, keyboards, gloves, tactile mouse, dance pads, exercise equipment, or other input devices. These devices are generally used by a user to control aspects of a game or other parameter of a computer program. Each of these input devices could also be configured to affect the room lights. For example, a mouse could be used to control the lights in a room. As the mouse is moved the lights in the room could respond, or as the user dances on a dance pad the lights could generate a color representation of their dance. For instance, their impact force with the pad could translate to an intensity while their position translated to a color. The input device may also direct sound simultaneously or in conjunction with the light.

In an embodiment of the invention the lighting system could also be associated with room inputs that could be associated with the virtual environment such as a microphone, camera, heat, cooling or other room inputs. For example, a user could control a game object by providing voice instructions through the microphone, which could be synthesized into commands for an application, and in turn used to control the illumination of the environment through a lighting system.

The embodiments discussed above relate primarily to games involving real-time simulation and for such types of games there are numerous applications for lighting systems. For instance: flight games could use indicators for controls or important statistics like fuel level; racing games could have motion or indicate third party activities like the approach of police vehicles: skateboarding, snowboarding, or other performance sport simulators can have indicators of movement, indicators of third party actions, or rewards such as flashbulbs for particularly fine performances. Other types of simulators can use lighting systems including, but not limited to, rollercoaster simulations, closed booth arcade simulators, or location-based entertainment games (large games inside a booth with multiple players). Further, it would be understood by one of skill in the art that the above are merely a limited overview of possibilities and there are many more applications that could be performed without undue experimentation.

Figure 15:
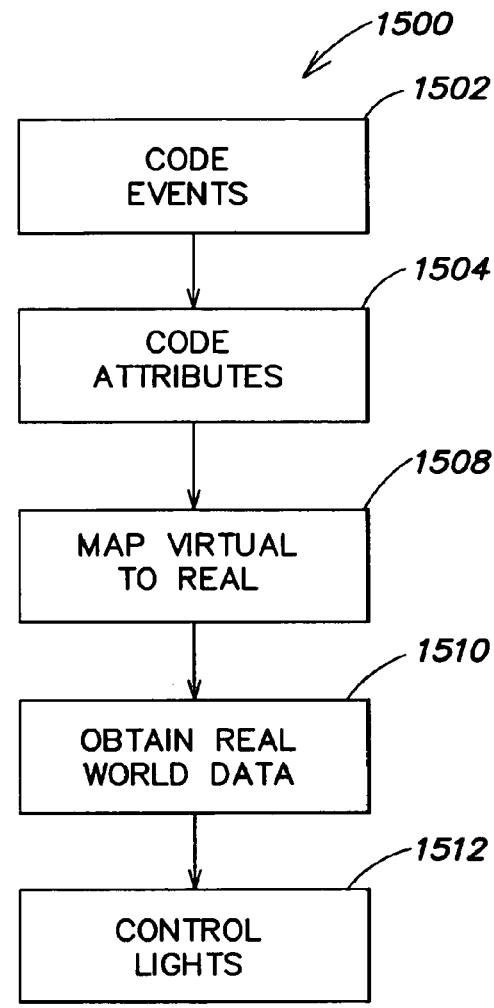
FIG. 15 shows a flow diagram for coordinated control of real world lights that are mapped to lights in a virtual lighting environment.

Simulation types of games are typically 3D rendered and have objects with attributes as well as events. Referring to the flow chart 1500 of FIG. 15, at a step 1502 a programmer can code events into the game. At a step 1504 a programmer can also code attributes or objects. Thus, a game program can track events and attributes, such as explosions, bullets, health, other people, patterns of light, and/or secret passageways. At a step 1508, the code can then map from the virtual world to the real world. In embodiments, at an optional step 1510, the system can add to the virtual world with real world data, such as from sensors or input devices. Then, at a step 1512, the system can control real and virtual world objects in coordination with each other. Also, by using the light system as an indicator, it is possible to give information through the light system that aids the user in playing a game or otherwise interacting with a virtual environment. For example, a light could flash or change color to indicate the coming of an event that would otherwise be a surprise to a user who does not have the light system when playing the game. The indicator functions of the light system can be coupled with three dimensional sound (such as surround sound) to provide enhanced real world effects that relate to events and attributes in the virtual environment.

In other embodiments the lighting systems can be used in conjunction with puzzle games, a developer can create a room-puzzle using the light system in a room or other environment to create games with the lights. For example, the room lights can reflect the color of puzzle elements in the virtual world, creating a correspondence between the virtual and the real world puzzle elements. One can manipulate real-world elements without the display on the computer. (In embodiments, one can play a game, such as pong, with the actual lights using a joystick attached to the computer. The code for the game can provide the interactive aspects of the game, then hand control signals to the light system so that the lights act as game elements in the real world environment. For example, one can create an array of lights on the ceiling, which could send light elements across the room). The lights can act as "pixels" in an array on the ceiling, wall or floor. In embodiments, the arrays could be established in a variety of rooms, so that light output moves from room to room in response to the user's interaction with the input device or sensor of the computer game or other virtual environment. Light strips can be used for game elements, as can other light system configurations.

A real world light system can be used to respond to input from objects in classic arcade computer games, such as Pac-man, pong, asteroids, space invaders, breakout, and similar games, in each case enhancing the user experience by providing either aesthetic or indicator functions. Light systems can also be used with any other game type, such as casino simulators, video poker, sandbox games, railroad tycoon games, simulation games like Sim City, and the like.

In embodiments, light systems can be used with role-playing games, such as two-dimensional games like Diablo and three-dimensional games like EverQuest (a massively multi-player online game). In such games, real world lights can be mapped to attributes of humans or objects in real world. The lights can provide more interaction with other humans or non-human players. Attributes and events can be a wide variety of things, such as indicating health, casting a spell, indicating shield strength or presence, displaying a fireball, or other effects. Further, in multiplayer games at a single location, the lights can be used to provide functions to the players by indicating the seat of a player you would like to meet in person, for example.

Further, in many multi player games (such as Everquest) items and characters have become collectible. Everquest Avatars are popular where there are characters that have characteristics that are acquired over time. Some are sold for large amounts of money on the Internet. The room lights of a light system can reflect the attributes of an avatar, such as a powerful blue to represent a "good" character, or a dark red to reflect "evil." Any attribute, ranging from personality traits, to strength, speed, location, health, constitution, intelligence, stamina, wisdom, or other attributes can be reflected for a given avatar by the room lights in the real world in correspondence to the attributes of the avatar in the virtual world. In embodiments, one can make collectible patterns or effects that associate with characters, objects or events. Thus, a virtual world object or character could have a "signature" or "trademark" color effect that takes place each time the character appears in the virtual world or does a particular thing in the virtual world. You could accrue an aura for a character over time as part of a character's attributes. Light could be used to portray abstract character traits. In multi-player environments like arcades, people could glow according to the aura of the character they are playing. Objects could embody those traits, and you might need to have a particular object or trait to allow you to see the indicator for another object.

In adventure games, which typically involve solving a puzzle in an environment—environmental lighting could be part of the puzzle. The light system could give clues required or helpful to solve the puzzle.

In sports games, a light system in the real world can serve as an event indicator (flashbulbs, cut scenes—could shift lights) or as an attribute indicator (indicating health of a player, number of fouls, etc.).

In turn-based strategy games, a light system can indicate events or attributes, or provide aesthetic effects. Those could include the day and night cycle, something catching fire (where the user sees the event first in the lights, then in virtual world), a warning from behind that comes first (such as to indicate a glowing light sabre of a player behind the user in the virtual world), or other events or attributes.

In fighting games, lights in the real world can indicate seeing someone's shadow before they jump over the user, moving lights after a "kill" or powerful blow, or indicating declining or improving health or presence of special attributes (such as shields or spells). Further, moving shadows or illumination created by the lights could indicate the position of a tag team partner. It is important to note that the absence of light (a shadow) can also be part of the illumination and illumination as described herein. The absence of any intensity of any color is simply ones possible illumination condition.

In children's games, room lights and a room sound system can reflect color and intensity attributes of elements of the games, which can include games to teach children about different colors and sounds.

As was discussed above, computer games provide merely one type of computer program in which a lighting system can provide enhancement and additional information. There are many other types of computer programs which the use of a lighting system can benefit A similar embodiment to computer games is auction-type, real "games," such as Internet auctions, such as E-bay. Lights could be used as an indicator of an event or characteristic, such as having the highest current bid, or a winning bid. Online gambling establishments could also use the lights so as to provide a casino-like environment in the user's home.

Figure 16:
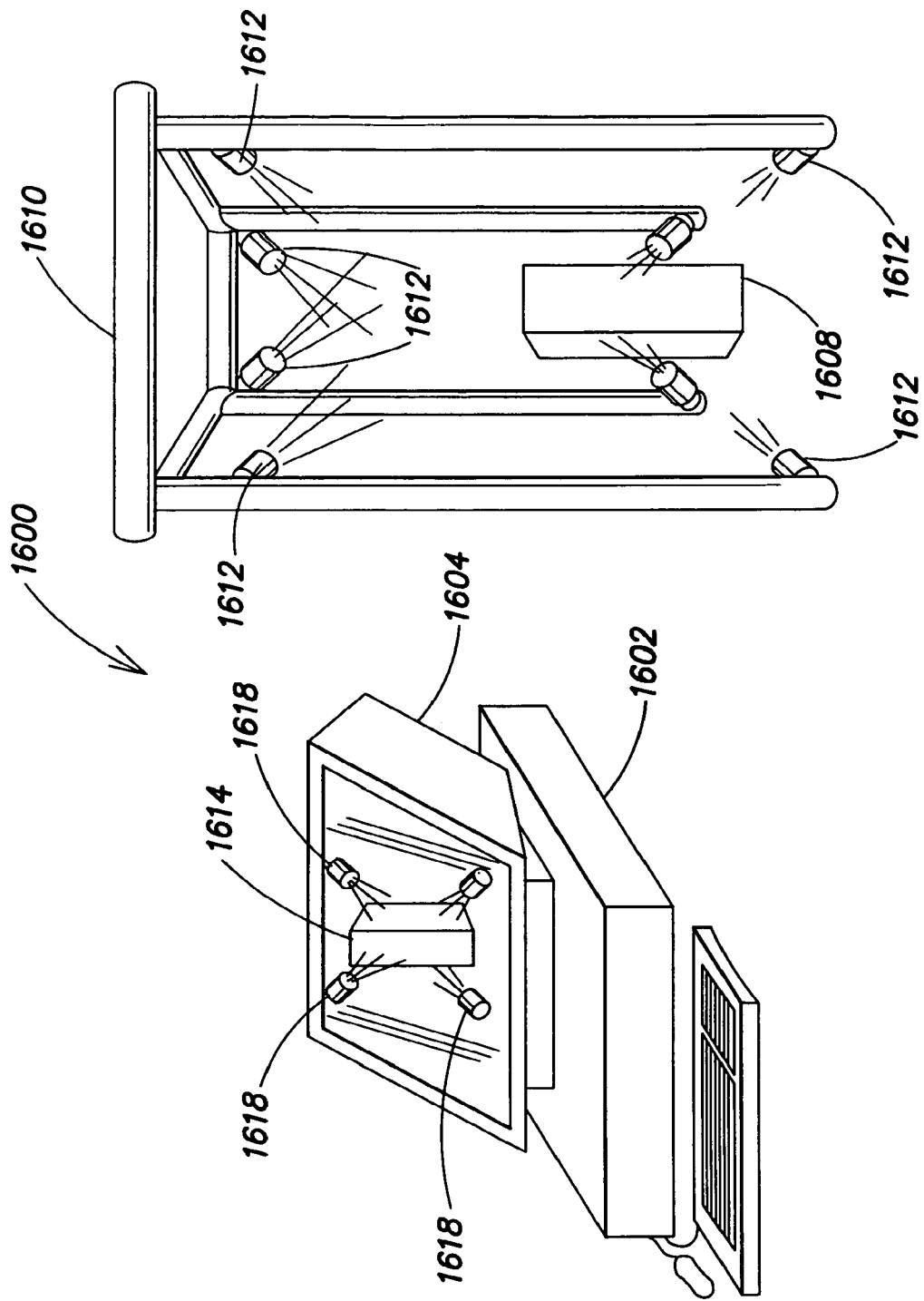
FIG. 16 shows a system for coordinating lighting with a computer application for simulating an architectural project.

Architectural visualization, mechanical engineering models, and other solid modeling environments are encompassed herein as embodiments. In these virtual environments lighting is often relevant both in a virtual environment and in a solid model real world visualization environment. Referring to FIG. 16, a system 1600 includes a computer 1602 with a display 1604. The system 1600 also includes a solid model 1608, as well as a lighting system 1610, with one or more lights 1612. The lighting system 1610 lights the solid model 1608 in the real world. A representation 1614 of the solid model can be created on the display screen, typically a three-dimensional representation created by a solid modeling program, such as those provided by SolidWorks. In the representation 1614 can be located virtual lights 1618, which can be represented as appearing in the modeling world in directions corresponding to the directions of the lights 1612 of the lighting system 1610. The user can thus position and control the light system to illuminate the real world solid model in correspondence to illumination conditions that are created in the virtual world environment. Scale physical models in a room of lights can be modeled for lighting during the course of a day or year or during different seasons for example, possibly to detect previously unknown interaction with the light and various building surfaces. Another example would be to construct a replica of a city or portion of a city in a room with a lighting system such as those discussed above. The model could then be analyzed for color changes over a period of time, shadowing, or other lighting effects. In an embodiment, this technique could be used for landscape design. In an embodiment, the lighting system is used to model the interior space of a room, building, or other piece of architecture. For example, an interior designer may want to project the colors of the room, or fabric or objects in the room with colors representing various times of the day, year, or season. In an embodiment, a lighting system is used in a store near a paint section to allow for simulation of lighting conditions on paint chips for visualization of paint colors under various conditions. These types of real world modeling applications can enable detection of potential design flaws, such as reflective buildings reflecting sunlight in the eyes of drivers during certain times of the year. Further, the three-dimensional visualization may allow for more rapid recognition of the aesthetics of the design by human beings, than by more complex computer modeling.

Solid modeling programs can have virtual lights. One can light a model in the virtual environment while simultaneously lighting a real world model the same way. For example, one can model environmental conditions of the model and recreate them in the real world modeling environment outside the virtual environment. For example, one can model a house or other building and show how it would appear in any daylight environment. A hobbyist could also model lighting for a model train set (for instance based on pictures of an actual train) and translate that lighting into the illumination for the room wherein the model train exists. Therefore the model train may not only be a physical representation of an actual train, but may even appear as that train appeared at a particular time. A civil engineering project could also be assembled as a model and then a lighting system according to the principles of the invention could be used to simulate the lighting conditions over the period of the day. This simulation could be used to generate lighting conditions, shadows, color effects or other effects. This technique could also be used in Film/Theatrical modeling or could be used to generate special effects in filmmaking. Such a system could also be used by a homeowner, for instance by selecting what they want their dwelling to look like from the outside and having lights be selected to produce that look. This is a possibility for safety when the owner is away. Alternatively, the system could work in reverse where the owner turns on the lights in their house and a computer provides the appearance of the house from various different directions and distances.

Although the above examples discuss modeling for architecture, one of skill in the art would understand that any device, object, or structure where the effect of light on that device, object, or structure can be treated similarly.

Medical or other job simulation could also be performed. A lighting system according to the principles of the present invention may be used to simulate the lighting conditions during a medical procedure. This may involve creating an operating room setting or other environment such as an auto accident at night, with specific lighting conditions. For example, the lighting on highways is generally high-pressure sodium lamps which produce nearly monochromatic yellow light and as a result objects and fluids may appear to be a non-normal color. Parking lots generally use metal halide lighting systems and produce a broad spectrum light that has spectral gaps. Any of these environments could be simulated using a system according to the principles of the invention. These simulators could be used to train emergency personnel how to react in situations lit in different ways. They could also be used to simulate conditions under which any job would need to be performed. For instance, the light that will be experienced by an astronaut repairing an orbiting satellite can be simulated on earth in a simulation chamber.

Lights can also be used to simulate travel in otherwise inaccessible areas such as the light that would be received traveling through space or viewing astronomical phenomena, or lights could be used as a three dimensional projection of an otherwise unviewable object. For instance, a lighting system attached to a computing device could provide a three dimensional view from the inside of a molecular model. Temporal Function or other mathematical concepts could also be visualized.

Optionally, the virtual environment can be generated by a computer application that is a screen saver, which could be mapped into the real world lights in a room. As the screen saver creates and displays graphics on a computer screen, for example, the screen saver can create lighting effects outside of the computer screen. This could be used to create decorative effects or the lighting effects could be used to provide information or other effects. The information may represent computer, or network activity, for example, such that the activity is displayed in the lights and or the screen saver. This could include email activity, when an email is received by the system the lighting could change to a particular hue, saturation or intensity. The hue, saturation or intensity may change as more and more email is received.

A musical application could also be used, allowing for the choreographing of music to light, or the generation of light as a portion of the generation of music. Alternatively light could be used to help a user learn to play music. For instance light could be projected that indicates a particular key a user should press on a keyboard. In time, a user unable to read music could teach themselves to play instruments and music for the user's performance could be provided as light signals.

An embodiment of the present invention could be a puzzle that consists of getting the room lights into a particular configuration. You could put a person "inside" a real world Rubik's cube associated with a virtual Rubik's cube. An embodiment of the invention may be used in flight simulators to change the ambient lighting conditions from day to night, or changing the lighting conditions as the horizon changes or associated with other aspects of the simulator.

A system according to the principles of the invention may also involve real-time simulation such as an actual motion inducing flight simulator, 3D motion rides (control through 3D libraries), or full mockup simulators where the lighting can be directly changed in response to what occurs. One example is that in a research submarine trainer the lighting within the submarine could be altered to remove red wavelengths as the sub dives because under water red light is often not present.

All articles, patents, and other references set forth above are hereby incorporated by reference. While the invention has been disclosed in connection with embodiments shown and described in detail, various equivalents, modifications, and improvements will be apparent to one of ordinary skill in the art from the above description DirectLight API A Programming Interface for Controlling Color Kinetics Full Spectrum Lighting Important Stuff You Should Read First 1) The sample program and Real Light Setup won't run until you register the DirectLight.dll COM object with Windows on your computer. Two small programs cleverly named "Register DirectLight.exe" and "Unregister DirectLight.exe" have been included with this install.

2) DirectLight assumes that you have a SmartJack hooked up to COM1. You can change this assumption by editing the DMX_INTERFACE_NUM value in the file "my_lights.h."

About DirectLight

Organization

An application (for example, a 3D rendered game) can create virtual lights within its 3D world. DirectLight can map these lights onto real-world Color Kinetics full spectrum digital lights with color and brightness settings corresponding to the location and color of the virtual lights within the game.

In DirectLights three general types of virtual lights exist:

Dynamic light. The most common form of virtual light has a position and a color value. This light can be moved and it's color changed as often as necessary. Dynamic lights could represent glowing space nebulae, rocket flares, a yellow spotlight flying past a corporate logo, or the bright red eyes of a ravenous mutant ice-weasel.

Ambient light is stationary and has only color value. The sun, an overhead room light, or a general color wash are examples of ambient. Although you can have as many dynamic and indicator lights as you want, you can only have one ambient light source (which amounts to an ambient color value).

Indicator lights can only be assigned to specific real-world lights. While dynamic lights can change position and henceforth will affect different real-world lights, and ambient lights are a constant color which can effect any or all real-world lights, indicator lights will always only effect a single real-world light. Indicators are intended to give feedback to the user separate from lighting, e.g. shield status, threat location, etc.

All these lights allow their color to be changed as often as necessary.

In general, the user will set up the real-world lights. The "my_lights.h" configuration file is created in, and can be edited by, the "DirectLight GUI Setup" program. The API loads the settings from the "my_lights.h" file, which contains all information on where the real-world lights are, what type they are, and which sort of virtual lights (dynamic, ambient, indicator, or some combination) are going to affect them.

Virtual lights can be created and static, or created at run time dynamically. DirectLights runs in it's own thread; constantly poking new values into the lights to make sure they don't fall asleep. After updating your virtual lights you send them to the real-world lights with a single function call. DirectLights handles all the mapping from virtual world to real world.

If your application already uses 3D light sources, implementing DirectLight can be very easy, as your light sources can be mapped 1:1 onto the Virtual_Light class.

A typical setup for action games has one overhead light set to primarily ambient, lights to the back, side and around the monitor set primarily to dynamic, and perhaps some small lights near the screen set to indicators.

The ambient light creates a mood and atmosphere. The dynamic lights around the player give feedback on things happening around him: weapons, environment objects, explosions, etc. The indicator lights give instant feedback on game parameters: shield level, danger, detection, etc.

Effects (LightingFX) can be attached to lights which override or enhance the dynamic lighting. In Star Trek: Armada, for example, hitting Red Alert causes every light in the room to pulse red, replacing temporarily any other color information the lights have.

Other effects can augment. Explosion effects, for example, can be attached to a single virtual light and will play out over time, so rather than have to continuously tweak values to make the fireball fade, virtual lights can be created, an effect attached and started, and the light can be left alone until the effect is done.

Real lights have a coordinate system based on the room they are installed in. Using a person sitting at a computer monitor as a reference, their head should be considered the origin. X increases to their right. Y increases towards the ceiling. Z increases towards the monitor.

Virtual lights are free to use any coordinate system at all. There are several different modes to map virtual lights onto real lights. Having the virtual light coordinate system axis-aligned with the real light coordinate system can make your life much easier.

Light positions can take on any real values. The DirectLight GUI setup program restricts the lights to within 1 meter of the center of the room, but you can change the values by hand to your heart's content if you like. Read about the Projection Types first, though. Some modes require that the real world and virtual world coordinate systems have the same scale.

Getting Started

Installing DirectLight SDK

Running the Setup.exe file will install:

In /Windows/System/ three dll files, one for DirectLight, two for low-level communications with the real-world lights via DMX.

DirectLight.dll
DMXIO.dll
DLPORTIO.dll

In the folder you installed DirectLight in: Visual C++ project files, source code and header files:

DirectLight.dsp
DirectLight.dsw
etc.
DirectLight.h
DirectLight.cpp
Real_Light.h
Real_Light.cpp
Virtual_Light.h
Virtual_Light.cpp
etc.

compile time libraries:

FX_Library.lib
DirectLight.lib
DMXIO.lib and configuration files:

my_lights.h
light_definitions.h
GUI_config_file.h
Dynamic_Localized_Strings.h

The "my_lights.h" file is referenced both by DirectLight and DirectLight GUI Setup.exe. "my_lights.h" in turn references "light_definitions.h" The other files are referenced only by DirectLight GUI Setup. Both the DLL and the Setup program use a registry entry to find these files:

HKEY_LOCAL_MACHINE\Software\ColorKinetics\
DirectLight\1.00.000\location

Also included in this directory is this documentation, and subfolders:

FX_Libraries contain lighting effects which can be accessed by DirectLights.

Real Light Setup contains a graphical editor for changing info about the real lights.

Sample Program contains a copiously commented program demonstrating how to use DirectLight.

DirectLight COM

The DirectLight DLL implements a COM object which encapsulates the DirectLight functionality. The DirectLight object possesses the DirectLight interface, which is used by the client program.

In order to use the DirectLight COM object, the machine on which you will use the object must have the DirectLight COM server registered (see above: Important Stuff You Should Read First). If you have not done this, the Microsoft COM runtime library will not know where to find your COM server (essentially, it needs the path of DirectLight.dll).

To access the DirectLight COM object from a program (we'll call it a client), you must first include "directlight.h", which contains the definition of the DirectLight COM interface (among other things) and "directlight_i.c", which contains the definitions of the various UIDs of the objects and interfaces (more on this later).

Before you can use any COM services, you must first initialize the COM runtime. To do this, call the CoInitialize function with a NULL parameter:

CoInitialize (NULL);

For our purposes, you don't need to concern yourself with the return value.

Next, you must instantiate a DirectLight object. To do this, you need to call the CoCreateInstance function. This will create an instance of a DirectLight object, and will provide a pointer to the DirectLight interface:

```
HRESULT hCOMError =
    CoCreateInstance(   CLSID_CDirectLight,
                        NULL,
                        CLSCTX_ALL ,
                        IID_IDirectLight,
                        (void **) &pDirectLight);
```

CLSID_CDirectLight is the identifier (declared in directlight_i.c) of the DirectLight object, IID_IDirectLight is the identifier of the DirectLight interface, and pDirectLight is a pointer to the implementation of the DirectLight interface on the object we just instantiated. The pDirectLight pointer will be used by the rest of the client to access the DirectLights functionality.

Any error returned by CoCreateInstance will most likely be REGDB_E_CLASSNOTREG, which indicates that the class isn't registered on your machine. If that's the case, ensure that you ran the Register DirectLight program, and try again.

When you're cleaning up your app, you should include the following three lines:

// kill the COM object pDirectLight->Release ( );
// We ask COM to unload any unused COM Servers. CoFreeUnusedLibraries ( );
// We're exiting this app so shut down the COM Library.
CoUninitiaiize ( )

You absolutely must release the COM interface when you are done using it. Failure to do so will result in the object remaining in memory after the termination of your app.

CoFreeUnusedLibraries( ) will ask COM to remove our DirectLight factory (a server that created the COM object when we called CoCreateInstance( )) from memory, and CoUninitialize( ) will shut down the COM library.

DirectLight Class

The DirectLight class contains the core functionality of the API. It contains functionality for setting ambient light values, global brightness of all the lights (gamma), and adding and removing virtual lights.

Types:
  enum Projection_Type{
    SCALE_BY VIRTUAL_DISTANCE_TO_CAMERA_ONLY=0,
    SCALE_BY_DISTANCE_AND_ANGLE=1,
    SCALE_BY_DISTANCE_VIRTUAL_TO_REAL=2};
  For an explanation of these values, see "Projection Types" in Direct Light Class
  enum Light_Type{
    C_75=0,
    COVE_6=1};
  For an explanation of these values, see "Light Types" in Direct Light Class, or look at the online help for "DirectLight GUI Setup."
  enum Curve_Type {
    DIRECTLIGHT_LINEAR=0,
    DIRECTLIGHT_EXPONENTIAL=1,
    DIRECTLIGHT_LOGARITHMIC=2};
  These values represent different curves for lighting effects when fading from one color to another.

Public Member Functions:

| void Set_Ambient_Light( | int R, |
| | int G, |
| | int B ); |

The Set_Ambient_Light function sets the red, green and blue values of the ambient light to the values passed into the function. These values are in the range 0-MAX_LIGHT_BRIGHTNESS. The Ambient light is designed to represent constant or "Room Lights" in the application. Ambient Light can be sent to any or all real of the real-world lights. Each real world light can include any percentage of the ambient light.
  void Stir_Lights( void *user_data );
  Stir_Lights sends light information to the real world lights based on the light buffer created within DirectLights. The DirectLight DLL handles stirring the lights for you. This function is normally not called by the application

| Virtual_Light * Submit_Virtual_Light( | float xpos, |
| | float ypos, |
| | float zpos, |
| | int red, |
| | int green, |
| | int blue ); |

Submit_Virtual_Light creates a Virtual_Light instance. Its virtual position is specified by the first three values passed in, it's color by the second three. The position should use application space coordinates. The values for the color are in the range 0-MAX_LIGHT_BRIGHTNESS. This function returns a pointer to the light created.
  void Remove_Virtual_Light( Virtual_Light * bad_light );
  Given a pointer to a Virtual_Light instance, Remove_Virtual_Light will delete the virtual light.
  void Set_Gamma( float gamma );
  The Set_Gamma function sets the gamma value of the Direct Light data structure. This value can be used to control the overall value of all the lights, as every virtual light is multiplied by the gamma value before it is projected onto the real lights.
  void Set_Cutoff_Range( float cutoff_range );
  Set_Cutoff_Range sets the cutoff distance from the camera. Beyond this distance virtual lights will have no effect on real-world lights. Set the value high to allow virtual lights to affect real world lights from a long way away. If the value is small virtual lights must be close to the camera to have any effect. The value should be in application space coordinates.
  void Clear_All_Real_Lights( void );
  Clear_All_Lights destroys all real lights.
  void Project_All_Lights ( void );
  Project_All_Lights calculates the effect of every virtual on every real-world light, taking into account gamma, ambient and dynamic contributions, position and projection mode, cutoff angle and cutoff range, and sends the values to every real-world light.

| void Set_Indicator_Color( | int which_indicator, |
| | int red, |
| | int green, |
| | int blue ); |

Indicators can be assigned to any of the real world lights via the configuration file ( my_lights.h). Each indicator must have a unique non-negative integer ID. Set_Indicator_Color changes the color of the indicator designated by which_indicator to the red, green, and blue values specified. If Set_Indicator_Color is called with an indicator id which does not exist, nothing will happen. The user specifies which lights should be indicators, but note that lights that are indicators can still be effected by the ambient and dynamic lights.
  Indicator Get_Indicator( int which_indicator );
  Returns a pointer to the indicator with the specified value.
  int Get_Real_Light_Count ( void );
  Returns the number of real lights.
  void Get_My Lights_Location( char buffer[MAX_PATH] );
  Looks in the directory and finds the path to the "my_lights.h" file.
  void Load_Real_Light_Configuration( char * fullpath = NULL );
  Loads the "my_lights.h" file from the default location determined by the registry. DirectLight will create a list of real lights based on the information in the file.

| void Submit_Real_Light( | char * indentifier, |
| | int DMX_port, |
| | Projection_Type projection_type, |
| | int indicator_number, |
| | float add_ambient, |
| | float add_dynamic, |
| | float gamma, |
| | float cutoff_angle, |
| | float x, |
| | float y, |
| | float z ); |

Creates a new real light in the real world. Typically DirectLight will load the real light information from the "my_lights.h" file at startup.
  void Remove_Real_Light( Real_Light * dead_light );
  Safely deletes an instance of a real light.

Light GetAmbientLight ( void );
Returns a pointer to the ambient light.
bool RealLightListEmpty ( void );
Returns true if the list of real lights is empty, false otherwise.

Light Class

Ambient lights are defined as lights. Light class is the parent class for Virtual Lights and Real Lights. Member variables:

static const int MAX_LIGHT_BRIGHTNESS. Defined as 255

LightingFX_List * m_FX_currently_attached. A list of the effects currently attached to this light.

ColorRGB m_color. Every light must have a color! ColorRGB is defined in ColorRGB.h void Attach_FX( LightingFX * new_FX )
Attach a new lighting effect to this virtual light.
void Detach_FX( LightingFX * old_FX )
Detach an old lighting effect from this virtual light.

Real Lights

Real Light inherits from the Light class. Real lights represent lights in the real world. Member variables:

static const int NOT_AN_INDICATOR_LIGHT defined as −1.

char m_identifier[100] is the name of the light (like "overhead" or "covelight1"). Unused by DirectLight except as a debugging tool.

int DMX_port is a unique non-negative integer representing the channel the given light will receive information on. DMX information is sent out in a buffer with 3 bytes (red, green and blue) for each light. (DMX_port * 3) is actually the index of the red value for the specified light. DirectLight DMX buffers are 512 bytes, so DirectLight can support approximately 170 lights. Large buffers can cause performance problems, so if possible avoid using large DMX_port numbers.

Light_Type m_type describes the different models of Color Kinetics lights. Currently unused except by DirectLight GUI Setup to display icons.

float m_add_ambient the amount of ambient light contribution to this lights color. Range 0-1 float m_add_dynamic the amount of dynamic light contribution to this lights color. Range 0-1 float m_gamma is the overall brightness of this light. Range 0-1.

float m_cutoff_angle determines how sensitive the light is to the contributions of the virtual lights around it. Large values cause it to receive information from most virtual lights. Smaller values cause it to receive contributions only from virtual lights in the same arc as the real light.

Projection_Type m_projection_type defines how the virtual lights map onto the real lights.

SCALE_BY_VIRTUAL_DISTANCE_TO_CAMERA_ONLY this real light will receive contributions from virtual lights based solely on the distance from the origin of the virtual coordinate system to the position of the virtual light The virtual light contribution fades linearly as the distance from the origin approaches the cutoff range.

SCALE_BY_DISTANCE_AND_ANGLE this real light will receive contributions from virtual lights based on the distance as computed above AND the difference in angle between the real light and the virtual light. The virtual light contribution fades linearly as the distance from the origin approaches the cutoff range and the angle approaches the cutoff angle.

SCALE_BY_DISTANCE_VIRTUAL_TO_REAL this real light will receive contributions from virtual lights based on the distance in 3-space from real light to virtual light. This mode assumes that the real and virtual coordinate systems are identical. The virtual light contribution fades linearly as the distance from real to virtual approaches the cutoff range.

float m_xpos x, y, z position in virtual space.
float m_ypos
float m_zpos int m_indicator_number. If indicator is negative the light is not an indicator. If it is non-negative it will only receive colors sent to that indicator number.

Virtual Lights

Virtual Lights represent light sources within a game or other real time application that are mapped onto real-world Color Kinetics lights. Virtual Lights may be created, moved, destroyed, and have their color changed as often as is feasible within the application.

static const int MAX_LIGHT_BRIGHTNESS;

MAX_LIGHT_BRIGHTNESS is a constant representing the largest value a light can have. In the case of most Color Kinetics lights this value is 255. Lights are assumed to have a range that starts at 0

| void Set_Color( | int R, |
| | int G, |
| | int B  ); |

The Set_Color function sets the red, green and blue color values of the virtual light to the values passed into the function.

| void Set_Position( | float x_pos, |
| | float y_pos, |
| | float z_pos  ); |

The Set_Position function sets the position values of the virtual light to the values passed into the function. The position should use application space coordinates.

| void Get_Position( | float *x_pos, |
| | float *y_pos, |
| | float *z_pos  ); |

Gets the position of the light.

Lighting FX

Lighting FX are time-based effects which can be attached to real or virtual lights, or indicators, or even the ambient light. Lighting effects can have other effects as children, in which case the children are played sequentially.

static const int FX_OFF; Defined as −1.
static const int START_TIME; Times to start and stop the effect. This is a virtual value. The
static const int STOP_TIME; individual effects will scale their time of play based on the total.
void Set_Real_Time( bool Real_Time );

If TRUE is passed in, this effect will use real world time and update itself as often as Stir_Lights is called. If FALSE is passed in the effect will use application time, and update every time Apply-FX is called.

void Set_Time_Extrapolation ( bool extrapolate );
If TRUE is passed in, this effect will extrapolate it's value when Stir_Lights is called.
void Attach_FX_To_Light ( Light * the_light );
Attach this effect to the light passed in.

| void Detach_FX_From_Light ( | Light * the_light, |
| | bool remove_FX_from_light = true ); |

Remove this effect's contribution to the light. If remove_FX_from_light is true, the effect is also detached from the light.
The above functions also exist as versions to effect Virtual lights, Indicator lights (referenced either by a pointer to the indicator or it's number), Ambient light, and all Real Lights.

| void Start ( | float FX_play_time, |
| | bool looping = false ); |

Start the effect. If looping is true the effect will start again after it ends.
void Stop ( void );
Stop the effect without destroying it.
void Time_Is_Up ( void );
Either loop or stop playing the effect, since time it up for it.
void Update_Time ( float time_passed );
Change how much game time has gone by for this effect.
void Update_Real_Time ( void );
Find out how much real time has passed for this effect.
void Update_Extrapolated_Time ( void );
Change the FX time based on extrapolating how much application time per real time we have had so far.
virtual void Apply_FX ( ColorRGB &base_color );
This is the principle lighting function. When Lighting_FX is inherited, this function does all the important work of actually changing the light's color values over time. Note that you can choose to add your value to the existing light value, replace the existing value with your value, or any combination of the two. This way Lighting effects can override the existing lights or simply supplant them.
static void Update_All_FX_Time ( float time_passed );
Update the time of all the effects.
void Apply_FX_To_All_Virtual_Lights ( void );
Apply this effect to all virtual, ambient and indicator lights that are appropriate.
void Apply_All_FX_To_All_Virtual_Lights ( void );
Apply each effect to all virtual, ambient and indicator lights that are appropriate.
void Apply_All_FX_To_Real_Light ( Real_Light * the_real_light );
Apply this effect to a single real light.
void Start_Next_ChildFX ( void );
If this effect has child effect, start the next one.
void Add_ChildFX ( LightingFX * the_child,
    float timeshare );
Add a new child effect onto the end of the list of child effects that this effect has. Timeshare is this child's share of the total time the effect will play. The timeshares don't have to add up to one, as the total shares are scaled to match the total real play time of the effect
void Become_Child_Of ( Lighting_FX * the_parent );
Become a parent of the specified effect.
void Inherit_Light_List ( Affected_Lights * our_lights );
Have this effect and all it's children inherit the list of lights to affect.

Configuration File

The file "my_lights.h" contains information about real-world lights, and is loaded into the DirectLight system at startup. The files "my_lights.h" and "light_definitions.h" must be included in the same directory as the application using DirectLights.
"my_lights.h" is created and edited by the DirectLight GUI Setup program. For more information on how to use the program check the online help within the program.
Here is an example of a "my_lights.h" file:

```
///////////////////////////////////////////////////////////
//
// my_lights.h
//
// Configuration file for Color Kinetics lights
//      used by DirectLights
//
// This file created with DirectLights GUI Setup v1.0
//
///////////////////////////////////////////////////////////
// Load up the basic structures
# include "Light_Definitions.h"
// overall gamma
float OVERALL_GAMMA = 1.0:
// which DMX interface do we use?
int DMX_INTERFACE_NUM = 0;
///////////////////////////////////////////////////////////
//
// This is a list of all the real lights in the world
//
Real_Light my_lights[MAX_LIGHTS] =
{
//NAME        PORT    TYPE    PRJ    IND    AMB     DYN     GAMMA   CUTOFF    X        Y        Z
"Overhead",   0,      1,      0,     -1,    1.000,  0.400,  1.000,  3.142,    0.000,   -1.000,  0.000,
"Left",       1,      0,      1,     -1,    0.000,  1.000,  1.000,  1.680,    -1.000,  0.000,   0.000,
"Right",      2,      0,      1,     -1,    0.000,  1.000,  0.800,  1.680,    1.000,   0.000,   0.000,
"Back",       3,      0,      1,     -1,    0.000,  1.000,  1.000,  1.680,    0.000,   0.000,   -1.000,
```

-continued

| | | | | | | | | | | |
|---|---|---|---|---|---|---|---|---|---|---|
| "LeftCove0", | 4, | 0, | 1, | 0, | 0.000, | 0.000, | 1.000, | 0.840, | −0.500, | −0.300, | 0.500, |
| "LeftCove1", | 5, | 0, | 1, | 1, | 0.000, | 0.000, | 1.000, | 0.840, | −0.500, | 0.100, | 0.500, |
| "LeftCove2", | 6, | 0, | 1, | −1, | 0.000, | 0.000, | 1.000, | 0.840, | −0.500, | 0.500, | 0.500, |
| "CenterCove0", | 7, | 0, | 1, | −1, | 0.000, | 0.000, | 1.000, | 0.840, | −0.400, | 0.700, | 0.500, |
| "CenterCove1", | 8, | 0, | 1, | −1, | 0.000, | 0.000, | 1.000, | 0.840, | −0.200, | 0.700, | 0.500, |
| "CenterCove2", | 9, | 0, | 1, | −1, | 0.000, | 0.000, | 1.000, | 0.840, | 0.200, | 0.700, | 0.500, |
| "CenterCove3", | 10, | 0, | 1, | −1, | 0.000, | 0.000, | 1.000, | 0.840, | 0.400, | 0.700, | 0.500, |
| "RightCove0", | 11, | 0, | 1, | 2, | 0.000, | 0.000, | 1.000, | 0.840, | 0.500, | 0.500, | 0.500, |
| "RightCove1", | 12, | 0, | 1, | −1, | 0.000, | 0.000, | 1.000, | 0.840, | 0.500, | 0.100, | 0.500, |
| "RightCove2", | 13, | 0, | 1, | −1, | 0.000, | 0.000, | 1.000, | 0.840, | 0.500, | −0.300, | 0.500, |
| }; | | | | | | | | | | | |

This example file is taken from our offices, where we had lights setup around a computer, with the following lights (referenced from someone sitting at the monitor): One overhead (mostly ambient); one on each side of our head (Left and Right); one behind our head; Three each along the top, left and right side of the monitor in front of us.

Each line in the "my_lights" file represents one Real_Light. Each Real_Light instance represents, surprise surprise, one real-world light.

The lower lights on the left and right side of the monitor are indicators 0 and 2, the middle light on the left side of the monitor is indicator 1.

The positional values are in meters. Z is into/out of the plane of the monitor. X is vertical in the plane of the monitor, Y is horizontal in the plane of the monitor.

MAX_LIGHTS can be as high as 170 for each DMX universe. Each DMX universe is usually a single physical connection to the computer (COM1, for example). The larger MAX_LIGHTS is, the slower the lights will respond, as MAX_LIGHTS determines the size of the buffer sent to DMX (MAX_LIGHTS * 3) Obviously, larger buffers will take longer to send.

OVERALL_GAMMA can have a value of 0-1. This value is read into DirectLights and can be changed during run-time.

We claim:

1. A method of controlling illumination in an environment of a visual display screen, comprising:
   providing an illumination source for producing illumination comprising a plurality of colors, wherein the illumination source comprises an array of LEDs;
   obtaining a signal related to content displayed on the display screen;
   providing a control system for controlling the illumination source, wherein the control system delivers a pulse-width modulated signal; and
   controlling the illumination source to illuminate the environment in coordination with the content displayed on the display screen.

2. A method of claim 1, wherein the content comprises objects in a computer game.

3. A method of claim 1, wherein the display screen has a housing and wherein the LEDs are disposed on the housing of the display screen.

4. A method of claim 3, wherein the network is a wireless network.

5. A method of claim 1, wherein obtaining the signal comprises obtaining code that is embedded in code for a computer game.

6. A method of claim 1, wherein obtaining the signal comprises detecting a signal directly from the display screen.

7. A method of claim 1, wherein obtaining the signal comprises obtaining a video signal through a video in port.

8. A method of claim 1, further comprising using the control system to control the illumination source in relation to a game object in a game.

9. A method of claim 8, wherein the control system controls the illumination source in coordination with disabling at least one function of the content displayed on the display screen.

10. A method of claim 9, wherein the display screen is entirely disabled for a period of time in coordination with control of the illumination source.

11. A method of claim 8, wherein the game object is an event and the illumination source is controlled to produce an effect that is related to the event.

12. A method of claim 11, wherein the event is an explosion and the effect is a flash.

13. A method of claim 11, wherein the event is a shot and the effect is a flash.

14. A method of claim 11, wherein the event is success and the effect is a flash.

15. A method of claim 11, wherein the event is approach of a threat and the effect is a color change.

16. A method of claim 11, wherein the event is a change in a characteristic of the game object and the effect is a color change.

17. A method of claim 11, wherein the event is movement and the effect is a wash of color.

18. A method of claim 11, wherein the event is movement and the effect is movement of color.

19. A method of claim 8, wherein the content is a game that provides a third person view and wherein the illumination source provides illumination that is an extension of the content displayed on the screen.

20. A method of claim 8, wherein the illumination source is controlled in coordination with a non-game object selected from the group consisting of the time of day, the end of the work day, the beginning of the work day, the beginning of a lunch period, sunset, sunrise, and an environmental condition.

21. A method of claim 8, further comprising controlling the illumination source to distract or deter the user of the content.

22. A method of claim 1, further comprising providing a surface located in proximity to the display screen for receiving illumination from the illumination source.

23. A method of claim 22, wherein the surface comprises an enclosure surrounding the display screen, a collapsible cabana, or a white surface.

24. A method of claim 22, wherein the surface comprises a graphical element that is adapted to be illuminated by the illumination source.

25. A method of claim 24, wherein altering the illumination from the illumination source creates an animation effect with the graphical element of the surface.

26. A method of claim 22, wherein the surface comprises a textured surface.

27. A method of claim 1, further comprising providing an audio system for producing sound that is related to the content.

28. A method of claim 27, further comprising controlling the illumination source to illuminate the environment of the display screen in coordination with the sound produced by the audio system.

29. A method of claim 27, wherein the audio system comprises speakers and the illumination source comprises a network of LEDs disposed in proximity to the speakers.

30. A method of claim 29, wherein the LEDs are disposed on the speakers.

31. A method of claim 1, wherein the display screen is a first display screen and the environment is a first environment, further comprising:
   providing a second display screen in a second environment,
   providing a second illumination source, and
   controlling the first and second illumination sources to coordinate illumination of the first and second environments in conjunction with the content displayed on the first and second display screens.

32. A method of claim 31, further comprising changing illumination in the second environment in coordination with content on the first display screen, wherein the first display screen and the second display screen display content for a multi-user computer game, and wherein illumination of the first environment and the second environment is coordinated in response to objects in the computer game.

33. A method of claim 32, wherein an event on the first display screen causes an illumination change in the second environment.

34. A method of claim 1, further comprising providing a mapping module for mapping a plurality of lights in the environment with a plurality of objects in the content.

35. A method of claim 34, further comprising mapping the plurality of lights in a home, to a plurality of lights in a virtual environment depicted on the display.

36. A method of claim 35, further comprising illuminating the lights in the home in coordination with the lights in the virtual environment.

37. A method of claim 1, further comprising providing a collapsible cabana for surrounding the display screen.

38. A method of claim 1, further comprising providing an indicator light disposed in proximity to the display screen.

39. A method of claim 38, further comprising using the indicator light to indicate a condition.

40. A method of claim 1, further comprising using data from the real world to influence at least one of an event, an object and an attribute in a virtual world in coordination with control of the illumination source.

41. A method of providing illumination in coordination with display of content on a display screen, comprising:
   displaying computer game content on a the display screen;
   providing an illumination source for illuminating an environment that is related to the display screen, the illumination source adapted to generate a plurality of colors, wherein the illumination source comprises a plurality of light emitting diodes, wherein the light emitting diodes are disposed in a network configuration, and wherein the light emitting diodes are controlled by pulse width modulation; and
   coordinating the illumination source to illuminate the environment in relationship to the computer game content on the display screen in response to a signal obtained from a computer game.

42. A method of claim 41, further comprising providing a surface in the environment of the display screen for accepting illumination from the illumination source.

43. A method of claim 42, wherein the surface comprises an enclosure.

44. A method of claim 43, wherein the enclosure is collapsible and portable.

45. A method of claim 42, wherein the surface comprises elements suitable for interacting with the illumination from the illumination source.

46. A method of claim 45, wherein the elements comprise graphical objects related to objects in the computer game.

47. A method of claim 41, further comprising providing a mounting apparatus for the illumination source.

48. A method of claim 47, wherein the mounting apparatus is collapsible.

* * * * *